United States Patent [19]

Warshawsky et al.

[11] Patent Number: 5,591,739
[45] Date of Patent: Jan. 7, 1997

[54] 2-SUBSTITUTED INDANE-2-CARBOXYALKYL DERIVATIVES USEFUL AS INHIBITORS OF ENKEPHALINASE AND ACE

[75] Inventors: Alan M. Warshawsky; Gary A. Flynn, both of Cincinnati, Ohio

[73] Assignee: Merrell Pharmaceuticals Inc., Cincinnati, Ohio

[21] Appl. No.: 423,675

[22] Filed: Apr. 17, 1995

Related U.S. Application Data

[60] Division of Ser. No. 163,235, Dec. 6, 1993, Pat. No. 5,457,196, which is a continuation-in-part of Ser. No. 129,484, Sep. 29, 1993, abandoned, which is a continuation of Ser. No. 929,482, Aug. 20, 1992, abandoned, which is a continuation-in-part of Ser. No. 767,289, Sep. 27, 1992, abandoned.

[51] Int. Cl.$^6$ ..................... A61K 31/55
[52] U.S. Cl. ............ 514/214; 514/215; 514/217
[58] Field of Search ............... 514/214, 215, 514/217

[56] References Cited

U.S. PATENT DOCUMENTS

| | | | |
|---|---|---|---|
| 3,334,091 | 7/1967 | Houlihan | 260/243 |
| 3,334,095 | 8/1967 | Houluhan | 260/243 |
| 4,080,449 | 3/1978 | Croisier et al. | 424/244 |
| 4,320,057 | 3/1982 | Freed et al. | 260/239.3 B |
| 4,391,752 | 7/1983 | Crossley | 548/540 |
| 4,399,136 | 8/1983 | Hassall et al. | 540/501 |
| 4,415,496 | 11/1983 | Harris et al. | 260/239.3 B |
| 4,487,929 | 12/1984 | Hassall et al. | 540/501 |
| 4,512,924 | 4/1985 | Attwood et al. | 544/235 |
| 4,584,294 | 4/1986 | Ruyle | 514/214 |
| 4,658,024 | 4/1987 | Attwood et al. | 540/500 |
| 4,692,438 | 9/1987 | Hassall et al. | 548/112 |
| 4,716,232 | 12/1987 | Ternansky | 548/112 |
| 4,734,504 | 3/1988 | Holmes | 548/364 |
| 4,734,505 | 3/1988 | Holmes | 548/364 |
| 4,762,924 | 8/1988 | Hassall et al. | 540/501 |
| 4,772,701 | 9/1988 | Attwood et al. | 544/235 |
| 4,782,149 | 11/1988 | Lawton et al. | 540/500 |
| 4,785,093 | 11/1988 | Hassall et al. | 540/460 |
| 4,808,713 | 2/1989 | Attwood et al. | 540/487 |
| 4,824,832 | 4/1989 | Flynn et al. | 540/522 |
| 4,826,980 | 5/1989 | Hassall et al. | 544/224 |
| 4,973,585 | 11/1990 | Flynn et al. | 514/214 |
| 5,208,230 | 5/1993 | Flynn et al. | 544/235 |
| 5,238,932 | 8/1993 | Flynn et al. | 514/214 |

FOREIGN PATENT DOCUMENTS

| | | |
|---|---|---|
| 0128728 | 12/1984 | European Pat. Off. . |
| 0249224 | 12/1987 | European Pat. Off. . |
| 0249223 | 12/1987 | European Pat. Off. . |
| 0322914 | 12/1988 | European Pat. Off. . |
| 0481522 | 4/1992 | European Pat. Off. . |
| 0492369 | 7/1992 | European Pat. Off. . |
| 0533084 | 9/1992 | European Pat. Off. . |
| 0599444 | 6/1994 | European Pat. Off. . |
| 9108195 | 6/1991 | WIPO . |
| 9109840 | 7/1991 | WIPO . |
| 9302099 | 2/1993 | WIPO . |

OTHER PUBLICATIONS

Fournie–Zaluski, Marie–Claude et al., *J. Med. Chem.*, 1992 vol. 35, pp. 2473–2481.
Fournie–Zaluski, Marie–Claude et al., *J. Med. Chem.*, 1992 vol. 35, pp. 1259–1266.
French, John F., *Jour. of Pharm and Exper. Therapeutics*, vol. 268, No. 1, pp. 180–186, 1994.
W. H. Parsons et al. *Biochemical and Biophysical Research Communications* vol. 117, No. 1, 1993 (Nov. 30, 1983).
Flynn, et al., J. Am. Chem. Soc. 109, 7914 (1987).
Flynn, et al., Peptide Chemistry (1987); T. Shiba & Sakakibara (ed.), Protein Research Foundation, Osaka (1988).
Flynn, et al., Tetrahedron letters, vol. 31 (6), 815–88 (1990).
Attwood, et al., J. Chem. Soc. Perkin Trans. I, pp. 1011–1019 (1986).
Natoff, et al., Drugs of the Future, vol. 12 (5): 475–483 (1987).
Journal of Am. Coll. of Card. vol. 17, No. 6, pp. 137B–142B (May 1991).
Supplement I Cir. vol. 86(4) P. 1–220(0873) (Oct. 1992).
J. Med. Chem. 1992, 35, 823–832, Timothy D. Ocain et al.
Bioorganic and Medical Chem. Letters Vo. 1, 309, 1991.
Burkholder, et al. *Bioorganic and Medical Chem. Letters*, vol. 3, No. 2, pp. 231–234, 1993.
Flynn et al., *J. Med. Chem.* 1993, 36 2420–2423.

*Primary Examiner*—Mukund J. Shah
*Assistant Examiner*—Pavanaram K. Sripada
*Attorney, Agent, or Firm*—Charlotte L. Barney

[57] ABSTRACT

The present invention relates to novel 2-substituted indane-2-carboxyalkyl derivatives useful as inhibitors of enkephalinase and ACE.

11 Claims, No Drawings

2-SUBSTITUTED INDANE-2-CARBOXYALKYL DERIVATIVES USEFUL AS INHIBITORS OF ENKEPHALINASE AND ACE

This is a division, of application Ser. No. 08/163,235, filed Dec. 6, 1993 now U.S. Pat. No. 5,457,196, which is a CIP of application Ser. No. 08/129,484, filed Sep. 29, 1993, now abandoned: which is a continuation of application Ser. No. 07/929,482, filed Aug. 20, 1992, now abandoned; which is a CIP of application Ser. No. 07/767,289, filed Sep. 27, 1992 now abandoned.

BACKGROUND OF THE INVENTION

Enkephalinase or, more specifically, endopeptidase-24.11, is a mammalian ectoenzyme which is involved in the metabolic degradation of certain circulating regulatory peptides. This enzyme, which is a $Zn^{+2}$-metallopeptidase, exerts its effect by cleaving the extracellular peptides at the amino group of hydrophobic residues and thus inactivates the peptides as regulatory messengers.

Enkephalinase is involved in the metabolic degradation of a variety of circulating regulatory peptides including endorphins, such as β-endorphin and the enkephalins, atrial natriuretic peptide (ANP), and other circulating regulatory peptides.

Endorphins are naturally-occurring polypeptides which bind to opiate receptors in various areas of the brain and thereby provide an analgesic effect by raising the pain threshold. Endorphins occur in various forms including α-endorphin, β-endorphin, γ-endorphin as well as the enkephalins. The enkephalins, i.e., Met-enkephalin and Leu-enkephalin, are pentapeptides which occur in nerve endings of brain tissue, spinal cord and the gastrointestinal tract. Like the other endorphins, the enkephalins provide an analgesic effect by binding to the opiate receptors in the brain. By inhibiting enkephalinase, the metabolic degradation of the naturally-occurring endorphins and enkephalins are inhibited, thereby providing a potent endorphin-or enkephalin-mediated analgesic effect. Inhibition of enkephalinase would therefore be useful in a patient suffering from acute or chronic pain. Inhibition of enkephalinase would also be useful in providing an antidepressant effect and in providing a reduction in severity of withdrawal symptoms associated with termination of opiate or morphine administration. In addition, inhibition of enkephalinase would also be useful in the treatment of irritable bowel syndrome.

ANP refers to a family of naturally-occurring peptides which are involved in the homeostatic regulation of blood pressure, as well as sodium and water levels. ANPs have been found to vary in length from about 21 to about 126 amino acids with a common structural feature being one or more disulfide-looped sequences of 17 amino acids with various amino-and carboxy-terminal sequences attached to the cystine moiety. ANPs have been found to bind to specific binding sites in various tissues including kidney, adrenal, aorta, and vascular smooth muscle with affinities ranging from about 50 pico-molar (pM) to about 500 nanomolar (nM) [Needleman, *Hypertension* 7, 469 (1985)]. In addition, it is believed that ANPs bind to specific receptors in the brain and possibly serve as neuromodulator as well as a conventional peripheral hormones.

The biological properties of ANP involve potent diuretic/natriuretic and vasodilatory/hypotensive effects as well as an inhibitory effect on renin and aldosterone secretion [deBold, *Science* 230,767 (1985)]. By inhibiting enkephalinase, the metabolic degradation of the naturally-occurring ANP is inhibited, thereby providing a potent ANP-mediated diuretic, natriuretic, hypotensive, hypoaldosteronemic effects. Inhibition of enkephalinase would therefore be useful in a patient suffering from disease states characterized by abnormalities in fluid, electrolyte, blood pressure, intraocular pressure, renin, or aldosterone homeostasis, such as, but not limited to, hypertension, renal diseases, hyperaldosteronemia, cardiac hypertrophy, glaucoma and congestive heart failure.

In addition, the compounds of the present invention are inhibitors of Angiotensin-Converting Enzyme (ACE). ACE is a peptidyl dipeptidase which catalyzes the conversion of angiotensin I to angiotensin II. Angiotensin II is a vasoconstrictor which also stimulates aldosterone secretion by the adrenal cortex. Inhibition of ACE would therefore be useful in a patient suffering from disease states such as hypertension and congestive heart failure [See William W. Douglas, "Polypeptides—Angiotensin, Plasma Kinins, and Others", Chapter 27, in GOODMAN AND GILLMAN'S THE PHARMACOLOGICAL BASIS OF THERAPEUTICS, 7th edition, 1985, pp. 652–3, MacMillan Publishing Co., New York, N.Y.]. In addition, it has been disclosed that ACE inhibitors are useful in treating cognitive disorders [German Application No. 3901-291-A, published Aug. 3, 1989].

Bradykinin refers to a naturally-occurring peptide which is a very powerful vasodilator and causes increased capillary permeability. By inhibiting enkephalinase and ACE, the metabolic degradation of bradykinin is inhibited, thereby providing increased levels of bradykinin in the circulation.

In addition, the compounds of the present invention are useful as inhibitors of smooth cell proliferation. Smooth muscle cell proliferation in the intima of muscular arteries is a primary cause of vascular stenosis in arteriosclerosis, after vascular surgery, and after coronary angioplasy. Several animal studies have indicated the renin-angiotensin system plays an important role in this vascular response to injury. Chronic treatment with angiotensin converting enzyme (ACE) inhibitors reduced myointimal thickening following balloon injury in rat carotid artery or aorta. Powell, J. S., Muller R. K. M. and Baumgartner, H. R.; Suppression of the vascular response to injury: The role of angiotensin-converting enzyme inhibitors. J. Am. Coll. Cardiol. 17:137B-42B, 1991. More recently, atrial natruiuretic peptide (ANP) has been found to decrease myointimal proliferation. ANP is rapidly metabolized by receptor mediated clearance and by neutral endopeptidase (NEP). Inhibition of NEP significantly reduces proliferation in the balloon-injured rabbit vasculature. Davis, H. R., McGregor, D. C., Hoos, L., Mullins, D. E. and Sybertz, E. J.: Atrial naturiuretic factor and the neutral endopeptidase inhibitor SCH42495 prevent myointimal proliferation after vascular injury. Circ. 86:I-220, 1992. These studies imply that a dual inhibitor of ACE and NEP should be therapeutically useful in the treatment of conditions which require inhibition of smooth cell proliferation. Davis and Sybertz, European Patent Application 533084-A1, Mar. 24, 1993.

SUMMARY OF THE INVENTION

The present invention provides novel compounds of the Formula (I)

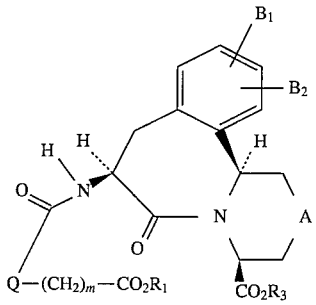

wherein $B_1$ and $B_2$ are each independently hydrogen; hydroxy; —$OR_2$ wherein $R_2$ is a $C_1$–$C_4$ alkyl or an Ar—Y group wherein Ar is aryl and Y is a hydrogen or $C_1$–$C_4$ alkyl; or, where $B_1$ and $B_2$ are attached to adjacent carbon atoms, $B_1$ and $B_2$ can be taken together with said adjacent carbons to form a benzene ring or methylenedioxy;

A is a bond, methylene, oxygen, sulfur, $NR_4$ or $NCOR_5$ wherein $R_4$ is hydrogen, a $C_1$–$C_4$ alkyl or an Ar—Y— group and $R_5$ is —$CF_3$ or a $C_1$–$C_{10}$ alkyl or an Ar—Y group;

$R_3$ is hydrogen or —$CH_2OC(O)C(CH_3)_3$;

$R_1$ is hydrogen, $C_1$–$C_4$ alkyl, or —$CH_2OC(O)C(CH_3)_3$;

m is an integer 1 to 3; and

Q is a group of the formula

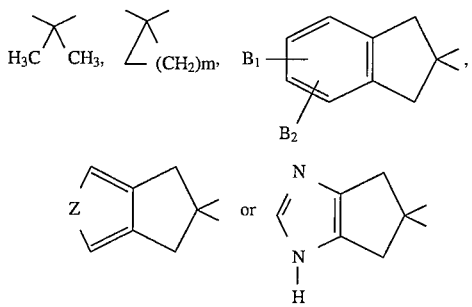

wherein Z is O, NH or S; and m is an integer 1 to 5.

The present invention further provides a method of inhibiting enkephalinase in a patient in need thereof comprising administering to said patient an effective enkephalinase inhibitory amount of a compound of Formula (I). The present invention also provides a method of inhibiting ACE in a patient in need thereof comprising administering to said patient an effective ACE inhibitory amount of a compound of Formula (I).

In addition, the present invention provides a composition comprising an assayable amount of a compound of Formula (I) in admixture or otherwise in association with an inert carrier. The present invention also provides a pharmaceutical composition comprising an effective inhibitory amount of a compound of Formula (I) in admixture or otherwise in association with one or more pharmaceutically acceptable carriers or excipients.

DETAILED DESCRIPTION OF THE INVENTION

As used herein, the term "$C_1$–$C_4$ alkyl" refers to a saturated straight or branched chain hydrocarbyl radical of one to four carbon atoms and includes methyl, ethyl, propyl, isopropyl, n-butyl, isobutyl, tertiary butyl and the like. The terms "$C_1$–$C_8$ alkyl" and "$C_1$–$C_{10}$ alkyl" refer to saturated straight or branched chain hydrocarbyl radicals of one to eight and one to ten carbon atoms, respectively, including methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like. The term "halogen", "halo", "halide" or "X" refers to a chlorine, bromine, or iodine atom.

As used herein, the term "Ar—Y—" refers to a radical wherein Ar is an aryl group and Y is a $C_0$–$C_4$ alkyl. The term "Ar" refers to a phenyl or naphthyl group unsubstituted or substituted with from one to three substituents selected from the group consisting of methylenedioxy, hydroxy, $C_1$–$C_4$ alkoxy, fluoro and chloro. The term "$C_0$–$C_4$ alkyl" refers to a saturated straight or branched chain hydrocarbyl radical of zero to four carbon atoms and includes a bond, methyl, ethyl, propyl, isopropyl, n-butyl, isobutyl, tertiary butyl and the like. Specifically included within the scope of the term "Ar—Y—" are phenyl, naphthyl, phenylmethyl or benzyl, phenylethyl, p-methoxybenzyl, p-fluorobenzyl and p-chlorobenzyl.

As used herein, the designation "$\sim$" refers to a bond to a chiral atom for which the stereochemistry is not designated and compounds of Formula I wherein A is a bond is understood to be a 5-membered ring.

The compounds of Formula I wherein A is a bond, methylene, oxygen, sulfur or NH can be prepared by utilizing procedures and techniques well known and appreciated by one of ordinary skill in the art. A general synthetic scheme for preparing these compounds is set forth in Scheme A wherein all substituents, unless otherwise indicated, are previously defined.

Scheme A

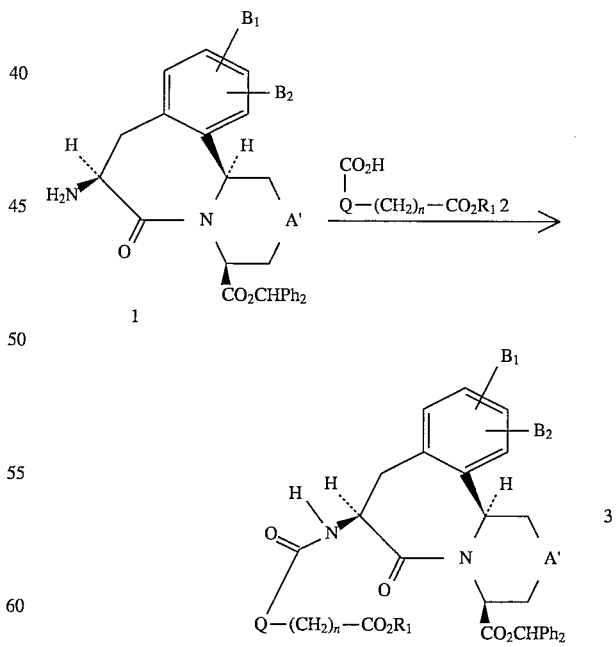

A' = a bond, —$CH_2$—, O, S or NH

The compounds of Formula I wherein A is a bond, methylene, oxygen, sulfur or NH can be prepared by reacting the appropriate ester/carboxylic acid compound of structure 2 with the appropriate amino compound of structure 1.

For example, the appropriate amino compound of structure 1 can be reacted with the appropriate ester/carboxylic acid compound of structure 2 in the presence of a coupling reagent such as EDC (1-(3-dimethylaminopropyl)-3-ethyl-carbodiimide hydrochloride), DCC (1,3-dicyclohexylcarbodiimide), or diethylcyanophosponate in a suitable aprotic solvent, such as methylene chloride to give the appropriate tricyclic compound of structure 3.

Alternatively, the ester/carboxylic acid compound of structure 2 can be converted to the corresponding ester/acid chloride, followed by reaction with the appropriate amino compound of structure 1 to give the appropriate compound of Formula I.

As summarized in Table 1, the $R_1$ and $R_3$ groups on the compounds Formula 1 can be manipulated using techniques and procedures well known and appreciated by one of ordinary skill in the art to give the corresponding compounds of structures 4 through 9.

For example, both the diphenylmethyl ester functionality and the t-butyl ester functionality of the appropriate tricyclic compound of structure 3, wherein $R_1$ is t-butyl and $R_3$ is diphenylmethyl, can be removed using trifluoroacetic acid to give the appropriate dicarboxylic acid compound of structure 4.

For example, the appropriate tricyclic compound of structure 3, wherein $R_1$ is t-butyl and $R_3$ is diphenylmethyl, is contacted in an appropriate acidic solvent such as trifluoroacetic acid. The reactants are typically stirred together at room temperature for a period of time ranging from 1–24 hours. The dicarboxylic acid compound of structure 4 is recovered from the reaction zone by extractive methods as is known in the art. It can be purified by silica gel chromatography.

Both the carboxylic acid functionalities of the appropriate dicarboxylic acid compound of structure 4 can be reesterified using techniques and procedures well known and appreciated in the art. For example, a dipivaloyloxymethyl ester compound of structure 5 can be prepared by treating the dicarboxylic acid compound of structure 4 with 2 molar equivalents of chloromethyl pivalate in a suitable aprotic solvent, such as dimethylformamide along with a non-nucleophilic base, such as cesium carbonate.

The diphenylmethyl ester functionality of the appropriate tricyclic compound of structure 3, wherein $R_1$ is $C_1$–$C_4$ alkyl and $R_3$ is diphenylmethyl can be selectively removed using catalytic hydrogenation as is known in the art to give the appropriate $C_1$–$C_4$ alkyl ester/carboxylic acid compound of structure 6. For example, the $C_1$–$C_4$ alkyl ester/carboxylic acid compound of structure 6 can be prepared by treating the appropriate tricyclic compound of structure 3, wherein $R_1$ is $C_1$–$C_4$ alkyl and $R_3$ is diphenylmethyl with a catalytic amount of palladium/carbon and a molar excess of ammonium formate. The reactants are typically contacted in a suitable polar organic solvent such as methanol. The reactants are typically contacted at room temperature for a period of time ranging from 3 minutes to 24 hours. The $C_1$–$C_4$ alkyl ester/carboxylic acid compound of structure 6 can be recovered from the reaction zone by filtration and evaporation of the solvent.

The carboxylic acid functionality of the appropriate $C_1$–$C_4$ alkyl ester/carboxylic acid compound of structure 6 can be reesterified to give the appropriate $C_1$–$C_4$ alkyl ester/pivaloyl methyl ether ester of structure 7. For example, a $C_1$–$C_4$ alkyl ester/pivaloyloxymethyl ester compound of structure 7 can be prepared by treating the appropriate $C_1$–$C_4$ alkyl ester/carboxylic acid compound of structure 6 with 1 molar equivalent of chloromethyl pivalate in a suitable aprotic solvent, Such as dimethylformamide along with a non-nucleophilic base, such as cesium carbonate.

The $C_1$–$C_4$ alkyl ester functionality of the appropriate $C_1$–$C_4$ alkyl ester/pivaloyl methyl ether ester of structure 7, wherein the $C_1$–$C_4$ alkyl ester is not t-butyl, can be hydrolyzed under basic conditions, such as lithium hydroxide in methanol, as is known in the art, to give the carboxylic acid/pivaloyl methyl ether ester of structure 8.

The compounds of Formula I wherein $R_1$ is pivaloyloxymethyl ester and $R_3$ is hydrogen can be prepared in a multi-step process.

For example, the $C_1$–$C_4$ alkyl ester functionality of the appropriate $C_1$–$C_4$ alkyl ester/diphenylmethyl ester of the appropriate tricyclic compound of structure 3, wherein the $C_1$–$C_4$ alkyl ester is not t-butyl can be hydrolyzed under basic conditions, such as lithium hydroxide in methanol, as is known in the art, to give the intermediate carboxylic acid/diphenylmethyl ester compound.

The carboxylic acid functionality of the appropriate intermediate carboxylic acid/diphenylmethyl ester compound can then be reesterified to give the intermediate pivaloyloxymethyl ester/diphenylmethyl ester compound. For example, an intermediate pivaloytoxymethyl/diphenylmethyl ester compound can be prepared by treating the appropriate intermediate carboxylic acid/diphenylmethyl ester compound with 1 molar equivalent of chloromethyl pivalate in a suitable aprotic solvent, such as dimethylformamide along with a non-nucleophilic base, such as cesium carbonate.

The diphenylmethyl ester functionality of the appropriate intermediate pivaloyloxymethyl/diphenylmethyl ester compound can be removed by hydrogenation as is known in the art to give the pivaloyloxymethyl/carboxylic acid compound of structure 9. For example, the pivaloyloxymethyl/carboxylic acid compound of structure 9 can be prepared by treating the appropriate intermediate pivaloyloxymethyl/diphenylmethyl ester compound with a catalytic amount of palladium/carbon and a molar excess of ammonium formate. The reactants are typically contacted in a suitable polar organic solvent such as methanol. The reactants are typically contacted at room temperature for a period of time ranging from 3 minutes to 24 hours. The pivaloyloxymethyl/carboxylic acid compound of structure 9 can be recovered from the reaction zone by filtration and evaporation of the solvent.

TABLE 1

MANIPULATION OF $R_1$ AND $R_3$

| Compound | $R_1$ | $R_3$ |
| --- | --- | --- |
| 4 | H | H |
| 5 | $CH_2OCOC(CH_3)_3$ | $CH_2OCOC(CH_3)_3$ |
| 6 | $C_1$–$C_4$ alkyl | H |
| 7 | $C_1$–$C_4$ alkyl | $CH_2OCOC(CH_3)_3$ |
| 8 | H | $CH_2OCOC(CH_3)_3$ |
| 9 | $CH_2OCOC(CH_3)_3$ | H |

The compounds of Formula I wherein A is —$NR_4$ can be prepared by techniques and procedures well known and appreciated by one of ordinary skill in the art. A general synthetic procedure for preparing these compounds is set forth in Scheme B. In Scheme B, all substituents unless otherwise indicated are as previously defined.

Scheme B

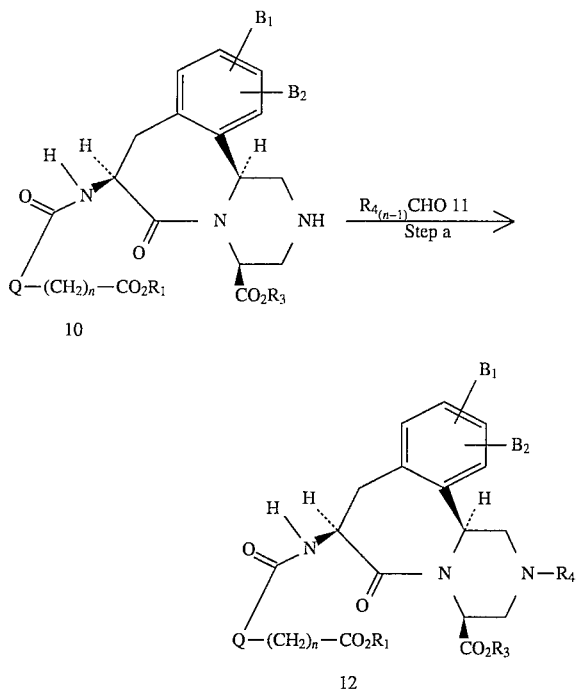

Scheme B provides a general synthetic procedure for preparing the compounds of Formula I wherein A is —NR$_4$. The amino functionality of the appropriate amino compound of structure 10 is subjected to reductive alkylation with the appropriate aldehyde of structure 11 using sodium cyanoborohydride, as is well known in the art, to give the corresponding N-alkylamino compound of structure 12.

The R$_1$ and R$_3$ groups on the compounds Formula 1 wherein A is —NR$_4$ can be manipulated as described previously in Scheme A and Table 1.

The compounds of Formula I wherein A is —NCOR$_5$ can be prepared by techniques and procedures well known and appreciated by one of ordinary skill in the art. A general synthetic procedure for preparing these compounds is set forth in Scheme C. In Scheme C, all substituents unless otherwise indicated are as previously defined.

Scheme C

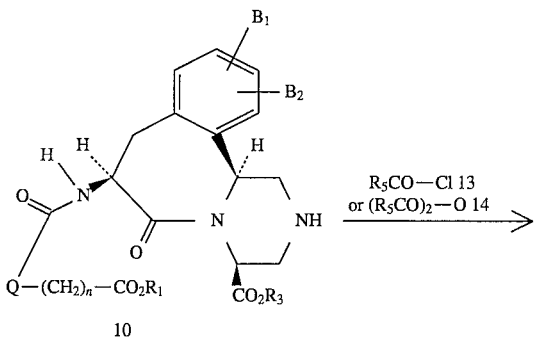

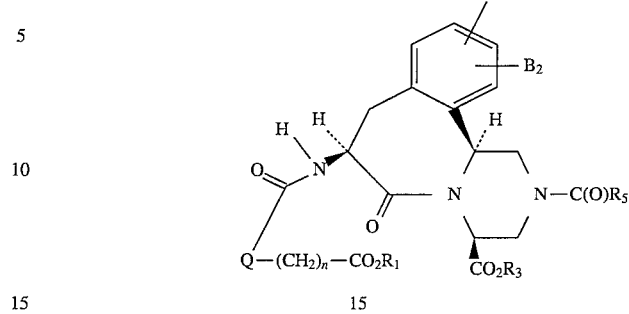

Scheme C provides a general synthetic procedure for preparing the compounds of Formula I wherein A is —NCOR$_5$. The appropriate amino compound of structure 10 is acylated using the appropriate acyl chloride of structure 13 or the appropriate anhydride of structure 14, as is well known in the art, to give the corresponding N-acylamino compound of structure 15.

The groups R$_1$ and R$_3$ may be manipulated by techniques and procedures well known and appreciated in the art and described previously in Scheme A and shown in Table 1.

Starting materials for use in Scheme A through Scheme C are readily available to one of ordinary skill in the art. For example, certain tricyclic amino compounds of structure 1 wherein X is S are described in European Patent 0 249 223 (Dec. 16, 1987) and certain other tricyclic amino compounds of structure 1 wherein A is methylene may be prepared as described in European Patent Application of Flynn and Beight, Application #34533A EP (Jun. 11, 1987).

Tricyclic amino compounds of structure 1 wherein A is O may be prepared as described in Scheme D. In Scheme D, all substituents unless otherwise indicated are as previously defined.

Scheme D

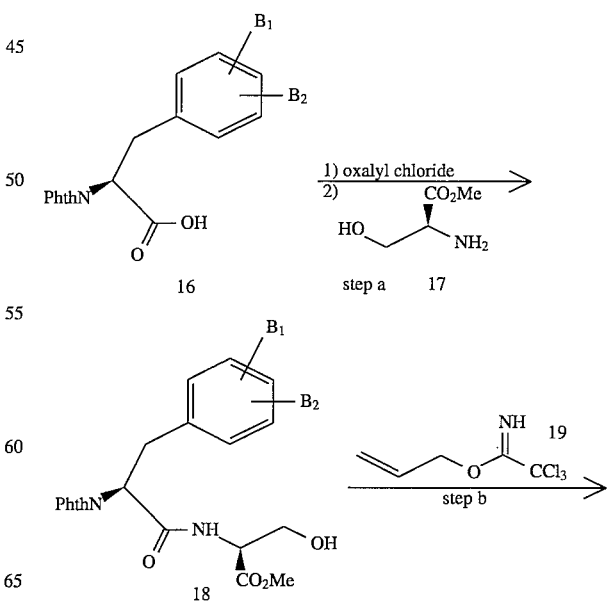

-continued
Scheme D

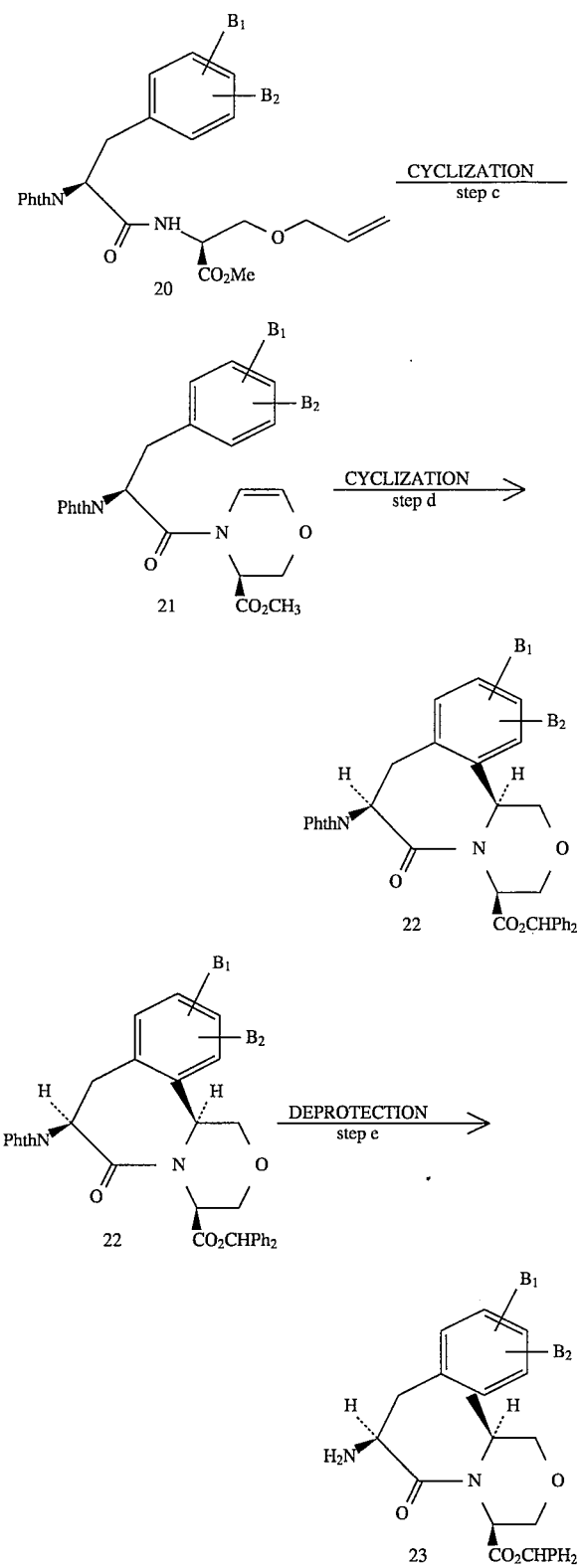

Scheme D provides a general synthetic procedure for preparing amino compounds of structure 1 wherein A is O.

In step a, the appropriate phthalimide blocked (S)-phenylalanine derivative of structure 16 is converted to the corresponding acid chloride, then reacted with the appropriate L-serine methyl ester of structure 17 to give the corresponding 1-oxo-3-phenylpropyl-L-serine methyl ester of structure 18.

For example, the appropriate phthalimide blocked (S)-phenylalanine derivative of structure 16 can be reacted with oxalyl chloride in a suitable aprotic solvent, such as methylene chloride. The resulting acid chloride can then be coupled with the appropriate L-serine methyl ester of structure 17 using N-methylmorpholine in a suitable aprotic solvent, such as dimethylformamide, to give the appropriate 1-oxo-3-phenylpropyl-L-serine methyl ester of structure 18.

In step b, the hydroxy functionality of the appropriate 1-oxo-3-phenylpropyl-L-serine methyl ester of structure 18 is allylated with the allyl imidate of structure 19 to give the corresponding 1-oxo-3-phenylpropyl-L-serine-O-allyl methyl ester of structure 20.

For example, the appropriate 1-oxo-3-phenylpropyl-L-serine methyl ester of structure 18 is contacted with 2 molar equivalents of the allyl imidate of structure 19 and a molar equivalent of a suitable acid such as trifluoromethanesulfonic acid. The reactants are typically contacted in a suitable organic solvent mixture such as methylene chloride/cyclohexane. The reactants are typically stirred together at room temperature under an inert atmosphere for a period of time ranging from 2–24 hours. The 1-oxo-3-phenylpropyl-L-serine-O-allyl methyl ester of structure 20 is recovered from the reaction zone by extractive methods as is known in the art. It may be purified by silica gel chromatography or crystallization.

In step c, the appropriate 1-oxo-3-phenylpropyl-L-serine-O-allyl methyl ester of structure 20 is cyclized to give the corresponding (4S)-enamine of structure 21.

For example, the appropriate 1-oxo-3-phenylpropyl-L-serine-O-allyl methyl ester of structure 20 is first contacted with a molar excess of a mixture of ozone/oxygen. The reactants are typically contacted in a suitable organic solvent mixture such as methylene chloride/methanol. The reactants are typically stirred together for a period of time ranging from 5 minutes to 30 minutes or until a blue color persists and at a temperature range of from −78° C. to −40° C. The reaction is quenched with an excess of methylsulfide and the intermediate aldehyde compound recovered from the reaction zone by extractive methods as is known in the art.

The intermediate aldehyde compound is then contacted with trifluoroacetic acid in a suitable aprotic solvent, such as methylene chloride to give the corresponding (4S)-enamine of structure 21.

In step d, the appropriate (4S)-enamine of structure 21 is cyclized to give the corresponding (4S)-tricyclic compound of structure 22 by an acid catalyzed Friedel-Crafts reaction. For example, the appropriate (4S)-enamine of structure 21 can be converted to the corresponding (4S)-tricyclic compound of structure 22 by treatment with a mixture of trifluoromethane sulfonic acid and trifluoroacetic anhydride in a suitable aprotic solvent, such as methylene chloride.

In step d, it may be necessary to reesterify the carboxy functionality due to the conditions of the work-up. For example, treatment of the crude product with bromodiphenylmethane in a suitable aprotic solvent, such as dimethylformamide along with a non-nucleophilic base, such as cesium carbonate, may be used to give the corresponding (4S)-diphenylmethyl ester.

In step e, the phthalimide protecting group of the appropriate (4S)-tricyclic compound of structure 22 is removed to give the corresponding amino compound of structure 23 wherein X is O. For example, the phthalimide protecting group of the appropriate (4S)-tricyclic compound of structure 22 can be removed using hydrazine monohydrate in a suitable protic solvent such as methanol, to give the corresponding (4S)-tricyclic amino compound of structure 23.

Tricyclic amino compounds of structure 1 wherein A is NH may be prepared as described in Scheme E. In Scheme E, all substituents unless otherwise indicated are as previously defined.

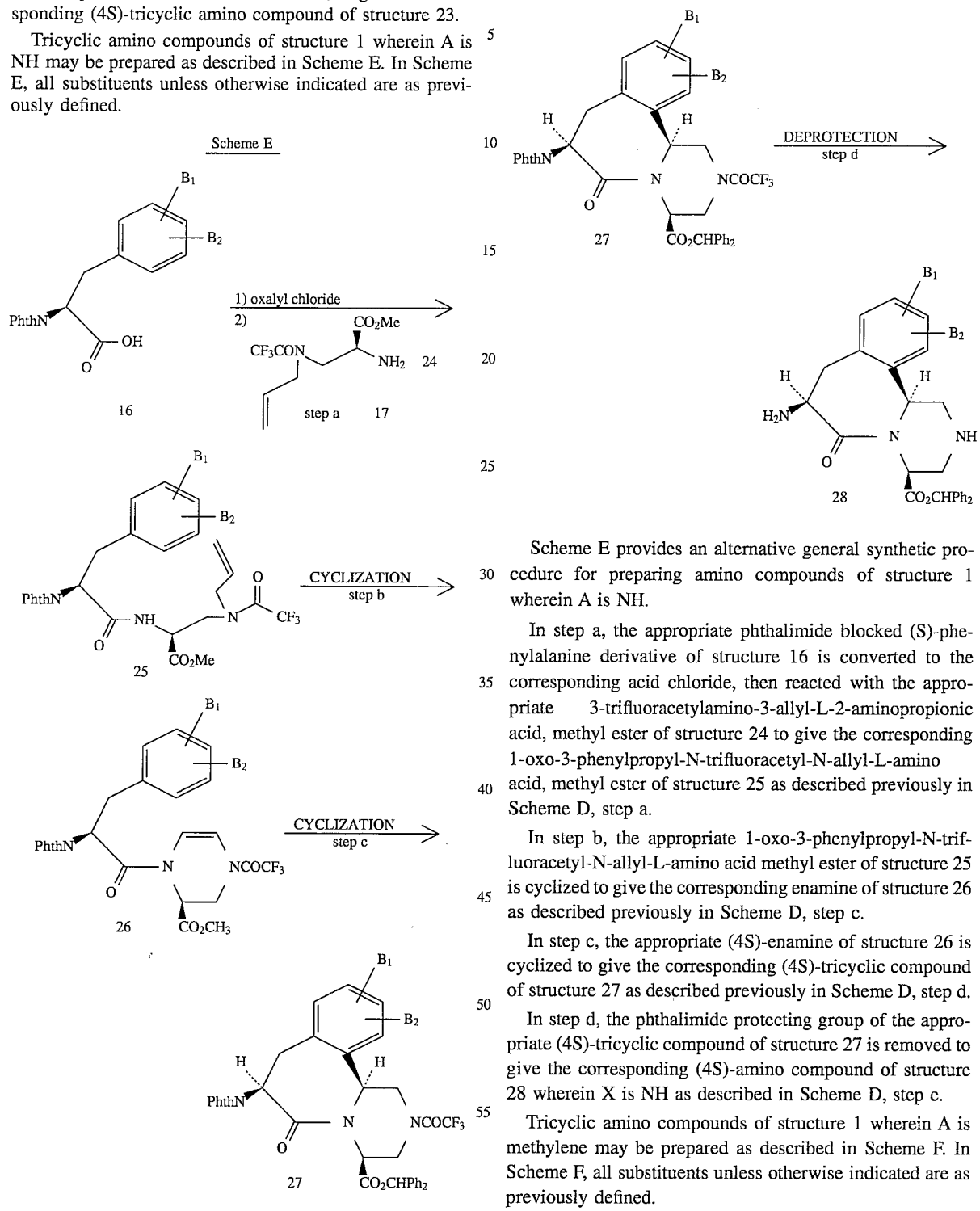

Scheme E provides an alternative general synthetic procedure for preparing amino compounds of structure 1 wherein A is NH.

In step a, the appropriate phthalimide blocked (S)-phenylalanine derivative of structure 16 is converted to the corresponding acid chloride, then reacted with the appropriate 3-trifluoracetylamino-3-allyl-L-2-aminopropionic acid, methyl ester of structure 24 to give the corresponding 1-oxo-3-phenylpropyl-N-trifluoracetyl-N-allyl-L-amino acid, methyl ester of structure 25 as described previously in Scheme D, step a.

In step b, the appropriate 1-oxo-3-phenylpropyl-N-trifluoracetyl-N-allyl-L-amino acid methyl ester of structure 25 is cyclized to give the corresponding enamine of structure 26 as described previously in Scheme D, step c.

In step c, the appropriate (4S)-enamine of structure 26 is cyclized to give the corresponding (4S)-tricyclic compound of structure 27 as described previously in Scheme D, step d.

In step d, the phthalimide protecting group of the appropriate (4S)-tricyclic compound of structure 27 is removed to give the corresponding (4S)-amino compound of structure 28 wherein X is NH as described in Scheme D, step e.

Tricyclic amino compounds of structure 1 wherein A is methylene may be prepared as described in Scheme F. In Scheme F, all substituents unless otherwise indicated are as previously defined.

Scheme F

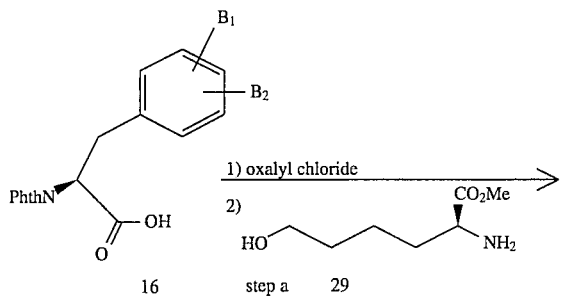

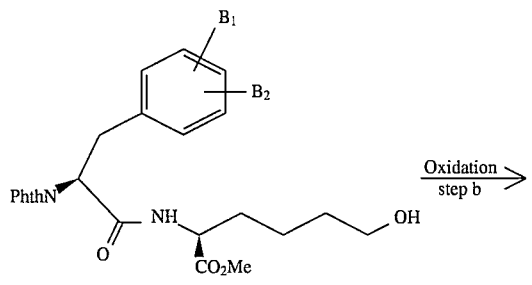

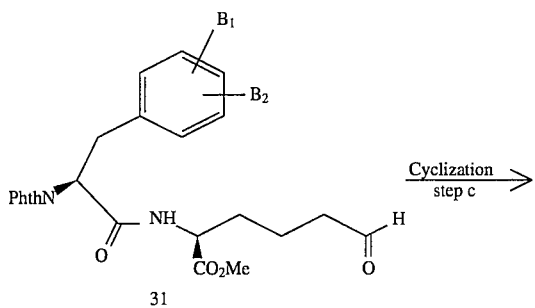

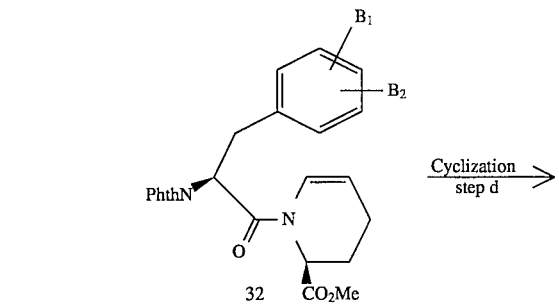

Scheme F provides a general synthetic procedure for preparing the tricyclo amino compounds of structure 1 wherein A is methylene.

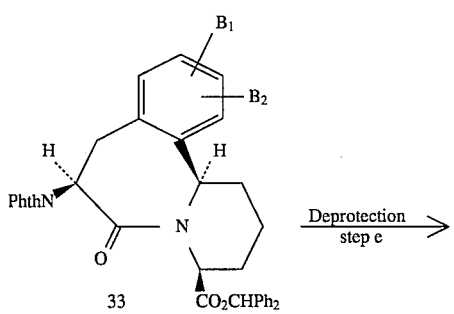

-continued
Scheme F

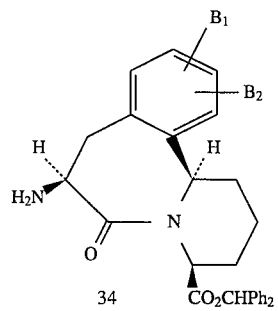

In step a, the appropriate phthalimide blocked (S)-phenylalanine derivative of structure 16 can be converted to the corresponding acid chloride, then reacted with the appropriate amino acid methyl ester of structure 29 in a coupling reaction. For example, the appropriate phthalimide blocked (S)-phenylalanine derivative of structure 16 can be reacted with oxalyl chloride in a suitable aprotic solvent, such as methylene chloride. The resulting acid chloride can then be coupled with the appropriate amino acid methyl ester of structure 29 using N-methylmorpholine in a suitable aprotic solvent, such as dimethylformamide, to give the appropriate 1-oxo-3-phenylpropyl-amino acid methyl ester derivative of structure 30.

In step b, the hydroxymethylene functionality of the appropriate 1-oxo-3-phenylpropyl-amino acid methyl ester derivative of structure 30 can be oxidized to the appropriate aldehyde of structure 31 by oxidation techniques well known and appreciated in the art. For example, the hydroxymethylene functionality of the appropriate 1-oxo-3-phenylpropyl-amino acid methyl ester derivative of structure 30 can be oxidized to the appropriate aldehyde of structure 31 by means of a Swern oxidation using oxalyl chloride and dimethylsulfoxide in a suitable aprotic solvent, such as methylene chloride.

In step c, the appropriate aldehyde of structure 31 can be cyclized to the appropriate enamine of structure 32 by acid catalysis. For example, the appropriate aldehyde of structure 31 can be cyclized to the appropriate enamine of structure 32 by treatment with trifluroacetic acid in a suitable aprotic solvent, such as methylene chloride.

In step d, the appropriate enamine of structure 32 can be converted to the corresponding tricyclic compound of structure 33 by an acid catalyzed Friedel-Crafts reaction. For example, the appropriate enamine of structure 32 can be converted to the corresponding tricyclic compound of structure 33 by treatment with a mixture of trifluoromethane sulfonic acid and trifluoroacetic anhydride in a suitable aprotic solvent, such as methylene chloride.

In step d, it may be necessary to reesterify the carboxy functionality due to the conditions of the work-up. For example, treatment of the crude product with bromodiphenylmethane in a suitable aprotic solvent, such as dimethylformamide along with a non-nucleophilic base, such as cesium carbonate, may be used to give the corresponding diphenylmethyl ester.

In step e, the phthalimide protecting group of the appropriate tricyclic compound of structure 33 can be removed using techniques and procedures well known in the art. For example, the phthalimide protecting group of the appropriate tricyclic compound of structure 33 can be removed using hydrazine monohydrate in a suitable protic solvent such as methanol, to give the corresponding amino compound of structure 34.

The compounds of Formula I wherein A is a bond can be prepared by utilizing procedures and techniques well known and appreciated by one of ordinary skill in the art. A general synthetic scheme for preparing these compounds is set forth in Scheme G wherein all substituents, unless otherwise indicated, are previously defined.

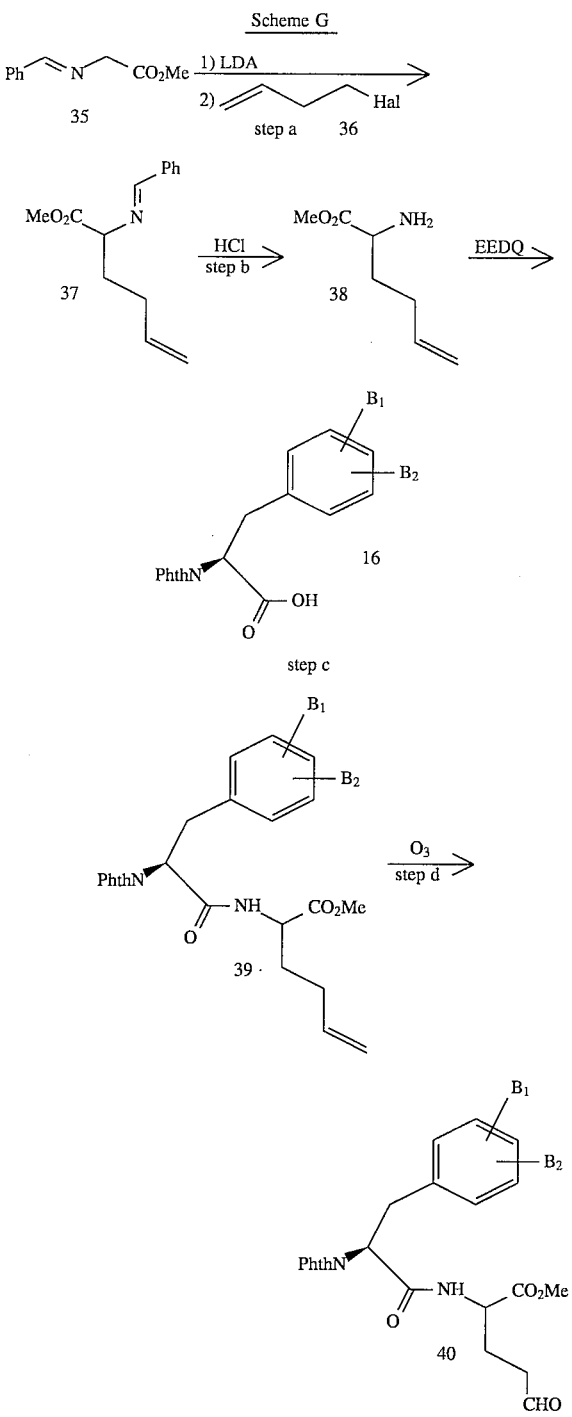

Scheme G provides a general synthetic procedure for preparing compounds of Formula I wherein A is a bond.

In step a, the N-(phenylmethylene)glycine methyl ester of structure 35 can be treated with one equivalent of a non-nucleophilic base, such as lithium diisopropylamide, in a suitable aprotic solvent, such as tetrahydrofuran, followed by addition of a 4-halobutene of structure 36 to give 2-(3-butenyl)-N-(phenylmethylene)glycine methyl ester of structure 37.

In step b, the N-(phenylmethylene) functionality of 2-(3-butenyl)-N-(phenylmethylene)glycine methyl ester of structure 37 can be hydrolyzed under acidic conditions, such as with hydrochloric acid in a suitable aprotic solvent, such as ethyl ether to give 2-(3-butenyl)-glycine methyl ester of structure 38.

In step c, the appropriate amide compound of structure 38 can be prepared by reacting the appropriate phthalimide protected (S)-phenylalanine compound of structure 16 with 2-(3-butenyl)-glycine methyl ester of structure 39 under coupling reaction conditions, such as with EEDQ, in a suitable aprotic solvent, such as methylene chloride.

In step d, the olefin functionality of the appropriate amide compound of structure 39 can be converted to the appropriate aldehyde compound of structure 40 under conditions of oxidative cleavage, such as treatment with ozone in a suitable solvent mixture, such as methylene chloride and methanol.

The compounds of Formula I wherein A is a bond can be prepared from an appropriate aldehyde of structure 40 in a process as outlined previously in Scheme F, steps c–e and Scheme A.

The individual 3(S) and 3(R) esters of the compounds of Formula I wherein A is a bond can be prepared from an appropriate aldehyde of structure 40 in a process as outlined previously in Scheme F, step c, separating the 3(S) and 3(R) esters of the enamine compounds formed from the cyclization reaction described in Scheme F, step c and completing the process as outlined in Scheme F, steps d–e and Scheme A.

The groups $R_1$ and $R_3$ may be manipulated by techniques and procedures well known and appreciated in the art and described previously in Scheme A and Table 1.

Starting materials for use in the general synthetic procedures outlined in Schemes D and F are readily available to one of ordinary skill in the art. For example, $N^\alpha$-(benzyloxycarbonyl)-β-(amino)-L-alanine is described in *J. Am. Chem. Soc.*, 107(24) 7105 1985, N-(phenylmethylene)glycine methyl ester is described in *J. Org. Chem.* 41, 3491 1976 and allyl trichloroacetimidate is described in *J. Chem. Soc. Perkin Trans.* 1(11) 2247 1985. 3,4-(Dicarboethoxy)thiophene is described in *Bull. Chem. Soc. Jpn.* 41 2532 1968 and 3,4-(dicarboethoxy)pyrrole is described in *Tetrahedron Lett.* 3165 1971.

The following examples present typical syntheses as described in Schemes A through G. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "mp" refers to melting point; "°C." refers to degrees Celsius; "mm Hg" refers to millimeters of mercury; "μL" refers to microliters; "μg" refers to micrograms; and "μM" refers to micromolar.

EXAMPLE 1

MDL 102,353

[4S-[4α, 7α(R*), 12bβ]]-7-[(2-Carboxymethyl-2-oxoindan)methylamino]-1,2,3,4,6,7,8,12b-octahydro-6-oxopyrido[2,1-a][2]benzazepine-4-carboxylic acid Scheme F, Step a: (S)-N-[2-(1,3-Dihydro-1,3-dioxo-2H-isoindol-2-yl)-1-oxo-3-phenylpropyl]-6-hydroxy-(S)-norleucine, methyl ester Mix phthalic anhydride (1.82 kgs, 12.3 mole), (S)-phenylalanine (1.84 kgs, 11.1 moles) and anhydrous dimethylformamide (2.26 L). Stir at 115°–120° C. for 2 hours under a nitrogen atmosphere. Pour into rapidly stirring water (32.6 L) and cool overnight at 0° C. Filter, wash with cold water (2×2 L) and air dry. Dissolve in a mixture of 9A ethanol (8.05 L) and water (8.05 L) and heat at reflux temperature. Gravity filter, cool to ambient temperature and refrigerate overnight at about 0° C. Filter the crystallized product, wash with cold 50:50 9A ethanol/water (2×2 L) and air dry to yield 2.96 kg (90.3%) of N-phthaloyl-(S)-phenylalanine; mp 177°–179° C.

Mix N-phthaloyl-(S)-phenylalanine (50.2 g, 0.17 mole), methylene chloride (660 mL) and dimethylformamide (0.5 mL) under a nitrogen atmosphere. Add oxalyl chloride (17.7 mL, 0.2 mole) over about 5 minutes with stirring. Stir at ambient temperature for 3 hours and evaporate the solvent in vacuo to leave N-phthaloyl-(S)-phenylalanine, acid chloride as a solid (54.3 g, 101.9%).

Mix 6-hydroxy-(S)-norleucine, methyl ester, hydrochloride salt (33.5 g, 0.1 mole) and dimethylformamide (201 mL), cool to about 0° C. and place under a nitrogen atmosphere. Add by dropwise addition, N-methylmorpholine (51 mL, 0.46 mole) with cooling so that the pot temperature stays at 0°–5° C. Stir at 0°–5° C. for an additional 10 minutes, than add a solution of N-phthaloyl-(S)-phenylalanine, acid chloride (53.5 g, 0.17 mole) in methylene chloride (270 mL) over 30 minutes with cooling so that the temperature stays at 0°–5° C. Remove the cooling bath and stir at room temperature for 18 hours.

Evaporate the methylene chloride in vacuo and dilute the remaining residue with ethyl acetate (800 mL). Extract the resulting mixture with water (800 mL), separate the organic layer and extract with 1N hydrochloric acid (270 mL), followed by water (3×500 mL). Dry the organic layer (MgSO$_4$), filter and evaporate in vacuo to yield crude product (76 g, 98%). Dissolve the crude product in hot toluene (223.5 mL), cool to room temperature, then cool overnight at about 0° C. Filter the crystallized product, wash with cold toluene and air dry to yield 56.6 g (76%) of the title compound; mp 128°–130° C.

Scheme F, Step b: 2-(1,3-Dihydro-1,3-dioxo-2H-isoindol-2-yl) 1-oxo-3-phenylpropyl-6-oxo-(S)-norleucine, methyl ester Mix oxalyl chloride (80 mL, 0.92 mole) and methylene chloride (2L) and place under a nitrogen atmosphere. Cool below −50° C. and add a solution of dimethyl sulfoxide (65.4 mL, 0.92 mole) in methylene chloride (425 mL). Stir for 15 minutes and add a solution of (S)-N-[2-(1,3-dihydro-1,3-dioxo-2H-isoindol-2-yl)-1-oxo-3-phenylpropyl]-6-hydroxy-(S)-norleucine, methyl ester (200 g, 0.456 mole) in methylene chloride (800 mL) over about 45 minutes, keeping the pot temperature below −50° C. for 30 minutes. Add triethylamine (420 mL, 3.01 mole) over 30 minutes. Stir while warming to 0° C. over 1.25 hours. Transfer the reaction mixture to a 12-liter flask. Stir and cool while adding a solution of OXONE (potassium peroxymonosulfate) (566 g) in water (6.74 L) at such a rate that the pot temperature stays below 15° C. Stir for 5 minutes, separate the organic layer and extract the aqueous layer with methylene chloride (1 L). Combine the organic phases, dry (MgSO$_4$) and filter to yield the title compound as a solution.

Scheme F, Step c: [S-(R*,R*)]-N-[2-(1,3-Dihydro-1,3-dioxo-2H-isoindol-2-yl)-1-oxo-3-phenylpropyl]-1,2,3,4-tetrahydro-2-pyridinecarboxylic acid, methyl ester Transfer the solution of 2-(1,3-dihydro-1,3-dioxo-2H-isoindol-2-yl)-1-oxo-3-phenylpropyl-6-oxo-(S)-norleucine, methyl ester in methylene chloride (volume about 4.5 L) to a 12-liter flask and place under a nitrogen atmosphere. Stir and add trifluoroacetic acid (440 mL, 5.71 mole) in one portion. Stir the resulting mixture at room temperature for one hour, then rapidly cool to about 0° C. Add a solution of sodium hydroxide (240 g, 6.0 mole) in water (3.4 L) in a slow stream to the vigorously stirred mixture at such a rate that the pot temperature stays at about 0° C. Separate the organic phase and extract the aqueous phase with methylene chloride (1 L). Combine the organic phases and dry (MgSO$_4$). Filter and remove the solvent in vacuo to leave a residue (262 g, 137%).

Dissolve the above residue in diethyl ether (1 L) and wash with water (5×500 mL). Evaporate the organic phase in vacuo to leave a residue of 229 g. Dilute the residue with methylene chloride (200 mL) and purify by silica gel chromatography (methylene chloride) to yield a viscous residue of 225 g.

Dilute the above residue with diethyl ether (250 mL) and allow to stand at room temperature for 24 hours. Filter the solid, wash with diethyl ether, and air dry to yield 123.2 g; mp 140°–142.5° C. Recrystallize (methylene chloride (125 mL)/isopropanol (615 mL)) by boiling off the solvent until the pot temperature reaches 75° C. and allowing the resulting sample to stand at room temperature for 24 hours. Filter, wash with cold isopropanol and air dry to yield 101.5 g of the title compound; mp 144°–146° C.

Evaporate the filtrate from the 101.5 g in vacuo to yield 24 g. Recrystallize (isopropanol) to yield an additional 3.5 g of the title compound.

Evaporate the filtrate from the 123.2 g in vacuo to leave 62 g of oil. Purify by silica gel chromatography (25% ethyl acetate/75% hexane), collecting 21–500 mL fractions. Combine fractions 9–20 and evaporate in vacuo to yield 35 g of a viscous oil. Recrystallize three times (isopropanol/5 mL/g) to yield an additional 11.9 g of the title compound; mp 142.5°–144.5° C. Total yield of useful material: 116.9 g (61.3%).

Scheme F, Step d: [4S-[4α, 7α(R*), 12bβ]]-7-[(1,3-Dihydro-1,3-dioxo-2H-isoindol-2-yl)]-1,2,3,4,6,7,8,12b-octahydro-6-oxopyrido-[2,1-a][2]benzazepine-4-carboxylic acid, diphenylmethyl ester Mix trifluoromethanesulfonic acid (500 g, 3.33 mole) and trifluoroacetic anhydride (74.8 mL, 0.53 mole) and place under a nitrogen atmosphere. Stir and add a solution of [S-(R*,R*)]-N-[2-(1,3-dihydro-1,3-dioxo-2H-isoindol-2-yl)-1-oxo-3-phenylpropyl]-1,2,3,4-tetrahydro-2-pyridinecarboxylic acid, methyl ester (200 g, 0.48 mole) in methylene chloride (1 L) with cooling at such a rate as to keep the pot temperature below 35° C. Stir at ambient temperature for 2 days. Pour into vigorously stirring ice water (5 L) and stir for 30 minutes. Extract with ethyl acetate (3×1 L), combine the organic phases and wash with water (3×500 mL). Evaporate in vacuo to a residue. Dissolve the residue in ethyl acetate (4 L) and extract with ¼ saturated potassium hydrogen carbonate (1 L), then ⅓ saturated potassium hydrogen carbonate (7×1 L). Combine the aqueous extracts and dilute with ethyl acetate (2 L). Stir the resulting mixture and cool to 5°–10° C. Adjust to pH 2 using concentrated hydrochloric acid (about 750 mL).

Separate the organic phase and extract the aqueous phase with ethyl acetate (3×1 L). Combine the ethyl acetate extracts, wash with water (3×1 L), then saturated sodium chloride (0.8 L), and dry (MgSO$_4$). Filter and wash with ethyl acetate (3×200 mL). Evaporate in vacuo to leave (188.3 g, 101.5%) [4S-[4α, 7α(R*), 12bβ]]-7-[(1,3-dihydro-1,3-dioxo-2H-isoindol-2-yl)]-1,2,3,4,6,7,8,12b-octahydro-6-oxopyrido[2,1-a][2]benzazepine-4-carboxylic acid as a colorless foam.

Dissolve [4S-[4α, 7α(R*), 12bβ]]-7-[(1,3-dihydro-1,3-dioxo-2H-isoindol-2-yl)]-1,2,3,4,6,7,8,12b-octahydro-6-oxopyrido[2,1-a][2]benzazepine-4-carboxylic acid (113.9 g, 0.28 mole) in methylene chloride (1.2 L) and dry over anhydrous MgSO$_4$ (60 g). Filter and wash with methylene chloride (3×200 mL). Evaporate in vacuo to a residue. Dissolve the residue in anhydrous dimethylformamide (860 mL) and place under a nitrogen atmosphere. Add cesium carbonate (98.9 g, 0.3 mole) in one portion. Stir for 45 minutes at ambient temperature. Add bromodiphenylmethane (164.8 g, 0.67 mole). Stir the resulting mixture at ambient temperature for 18 hours. Quench the reaction with ethyl acetate (2.464 L) and water (630 mL). Separate the organic phase and wash with water (7×625 mL), ¼ saturated potassium hydrogen carbonate (625 mL), water (625 mL), and saturated sodium chloride (625 mL). Dry (MgSO$_4$), filter and evaporate in vacuo to yield 214.4 g of an oil. Extract the combined aqueous washings with ethyl acetate (3×500 mL), wash with water (4×300 mL) and dry (MgSO$_4$). Filter and evaporate vacuo to yield an additional 20.2 g of an oil.

Dissolve the crude product (234.6 g) in methylene chloride (200 mL) and filter through a plug of silica gel (213 g), eluting with methylene chloride (2 L). Boil off the solvent and replace with hexane (3 L), with the pot temperature reaching a maximum of 65° C. Cool to ambient temperature, decant off the precipitated oil and crystallize (9A ethanol) to yield 96.6 g (60%) of the title compound; mp 153°–155° C.

Scheme F, Step e: [4S-[4α, 7α(R*), 12bβ]]-7-(Amino)-1,2,3,4,6,7,8,12b-octahydro-6-oxopyrido[2,1-a][2]benzazepine-4-carboxylic acid, diphenylmethyl ester Mix [4S-[4α, 7α(R*), 12bβ]]-7-[(1,3-dihydro-1,3-dioxo-2H-isoindol-2-yl)]-1,2,3,4,6,7,8,12b-octahydro-6-oxopyrido[2,1-a][2]benzazepine-4-carboxylic acid, diphenylmethyl ester (170.9 g, 0.3 mole), hydrazine monohydrate (34.4 g, 0.68 mole) and methanol (3.4 L) under a nitrogen atmosphere. Heat at reflux for 5 hours. Cool to ambient temperature and filter to remove phthaloyl hydrazide. Evaporate the filtrate in vacuo to a residue and slurry in chloroform (600 mL). Remove insoluble phthaloyl hydrazide by filtration and wash with chloroform (4×210 mL). Wash the filtrate with water (4×429 mL), dry (MgSO$_4$), and filter. Evaporate the filtrate to a solid residue of the title compound weighing 142 g (107.7%).

Scheme A: [4S-[4α, 7α(R*), 12bβ]]-7-[(2-Carboxymethyl-2-oxoindan)methylamino]-1,2,3,4,6,7,8,12b-octahydro-6-oxopyrido[2,1-a][2]benzazepine-4-carboxylic acid Dissolve diethylmalonate (15.2 mL, 0.100 mol) in tetrahydrofuran (800 mL). Cool in an ice bath and treat with sodium hydride (3.0 g, 0.10 mol, 80% in mineral oil). Stir until solution attained and add α,α'-dibromo-o-xylene (26.4 g, 0.100 mol). Stir for 30 minutes then add additional sodium hydride (3.0 g, 0.10 mol). Stir at room temperature for 20 hours, filter through filter aid and evaporate the solvent in vacuo. Purify by silica gel chromatography to give 2,2-(dicarboethoxy)indan as a pale yellow oil (16.0 g, 61.5%).

Dissolve 2,2-(dicarboethoxy)indan (15.9 g, 60.6 mmol) in dimethylsulfoxide (140 ml). Add water (14 mL) and lithium chloride (7.0 g, 0.16 mol). Heat at reflux for 4 hours, cool and partition between water (150 mL) and methylene chloride (2×150 mL). Wash the organic phase with water (150 mL), dry (MgSO$_4$) and pass through a silica gel plug to give 2-(carboethoxy)indan as an amber oil (6.49 g, 56%).

Dissolve 2-(carboethoxy)indan (6.49 g, 34.1 mmol) in ethanol (95%, 150 mL) and water (75 mL). Add potassium hydroxide (9.5 g, 0.17 mol) and stir at room temperature for 1 hour. Partition between water (150 mL) and ethyl ether (2×150 mL). Acidify the aqueous phase with hydrochloric acid to pH 1. Extract with methylene chloride (2×150 mL), dry (Na$_2$SO$_4$) and evaporate the solvent in vacuo to give 2-carboxyindanlic acid as a tan solid (3.82 g, 69%).

Dissolve 2-carboxyindanlic acid (3.82 g, 23.5 mmol) in methanol (60 mL) and treat with dimethoxypropane (5.8 mL, 47 mmol) and sulfuric acid (0.8 mL). Stir at room temperature for 15 hours. Evaporate the solvent in vacuo, dilute with methylene chloride (75 mL) and wash with saturated sodium hydrogen carbonate (35 mL). Extract the aqueous phase with methylene chloride (30 mL), wash combined organics with brine (30 mL) and dry (Na$_2$SO$_4$). Evaporate the solvent in vacuo and pass through a plug of silica gel to give 2-(carbomethoxy)indan as a yellow oil (3.98 g, 95.9%).

Dissolve diisopropylamine (0.88 mL, 6.28 mmol) in tetrahydrofuran (7.5 mL). Cool in an ice bath and add, by dropwise addition, n-butyllithium (3.6 mL of a 1.6M solution in hexanes, 5.75 mmol). Stir for 15 minutes, then cool to −78° C. Add a solution of 2-(carbomethoxy)indan (888 mg, 5.04 mmol) in tetrahydrofuran (5 mL). Stir for 45 minutes then add t-butyl bromoacetate (1.0 mL, 6.2 mmol). Stir for 3 hours, add saturated ammonium chloride (6 mL) and warm to room temperature. Partition between ethyl ether (75 mL) and water (10 mL). Dry (Na$_2$SO$_4$), evaporate the solvent in vacuo and purify by silica gel chromatography (7:1 hexane/ethyl acetate) to give 2-(carbomethoxy)-2-(carbo-t-butyloxymethyl)indan as a pale yellow solid (1.28 g, 73.1%).

Dissolve 2-(carbomethoxy)-2-(carbo-t-butyloxymethyl)indan (1.28 g, 4.4 mmol) in 95% ethanol (30 mL) and water (15 mL). Treat with potassium hydroxide (1.4 g, 25 mmol) and stir at room temperature for 3 hours. Add water (40 mL) and extract with ethyl ether (2×30 mL) and acidify the aqueous phase to pH 3 with solid tartaric acid. Extract with ethyl acetate (2×100 mL), dry (Na$_2$SO$_4$) and evaporate the solvent in vacuo to give 2-carboxy-2-(carbo-t-butyloxymethyl)indan as a pale yellow solid (1.08 g, 88.6%).

Dissolve [4S-[4α, 7α(R*), 12bβ]]-7-(amino)-1,2,3,4,6,7,8,12b-octahydro-6-oxopyrido[2,1a][2]benzazepine-4-carboxylic acid, diphenylmethyl ester (150 mg, 0.34 mmol) and EDC (98 mg, 0.50 mmol) in tetrahydrofuran (5 mL). Treat with 2-carboxy-2-(carbo-t-butyloxymethyl)indan (118 mg, 0.426 mmol). Stir at room temperature for 15 hours and evaporate the solvent in vacuo. Partition the residue between ethyl acetate (35 mL) and 1N hydrochloric acid (6 ml). Wash the organic phase with saturated sodium hydrogen carbonate (6 mL). Dry (Na$_2$SO$_4$) and evaporate the solvent in vacuo. Purify by silica gel chromatography (2:1 hexane/ethyl acetate) to give [4S-[4α, 7α(R*), 12bβ]]-7-[(2-(carbo-t- butyloxymethyl)-2-oxoindan)methylamino]-1,2,3,4,6,7,8, 12b-octahydro-6-oxopyrido[2,1-a][2]benzazepine-4-carboxylic acid, diphenylmethyl ester as a white solid (208 mg, 87.4%).

Dissolve [4S-[4α, 7α(R*), 12bβ]]-7-[(2-(carbo-t-butyloxymethyl)-2-oxoindan)methylamino]-1,2,3,4,6,7,8,12b-octahydro-6-oxopyrido[2,1-a][2]benzazepine-4-carboxylic acid, diphenylmethyl ester (205 mg, 0.293 mmol) in methylene chloride (3 mL) and cool to 0° C. Treat with trifluoroacetic acid (0.8 mL, 1 mmol) and anisole (0.2 mL 18 mmol) Stir at room temperature for 18 hours, dilute with ethyl acetate (50 mL) and wash with brine (2×15 mL). Dry (Na$_2$SO$_4$) and evaporate the solvent in vacuo. Purify by silica gel chromatography (2:1 hexane/ethyl acetate to 1:1 hexane/ethyl acetate with 5% acetic acid) to give the title compound as a white powder (110 mg, 78.6%).

EXAMPLE 2

[4S-[4α, 7α(R*), 12bβ]]-7-[(2-Pivaloyloxymethylcarboxymethyl)-2-oxoindan)methylamino]-1,2,3,4,6,7,8,12b-octahydro-6-oxopyrido[2,1-a][2]benzazepine-4-carboxylic acid, pivaloyloxymethyl ester Dissolve [4S-[4α, 7α(R*), 12bβ]]-7-[(2-carboxymethyl-2-oxoindan)methylamino]-1,2,3,4,6,7,8,12b-octahydro-6-oxopyrido[2,1-a][2]benzazepine-4-carboxylic acid (67 mg, 0.14 mmol) in methylene chloride (1 mL) and dry over anhydrous MgSO$_4$ (60 mg). Filter and wash with methylene chloride (3×20 mL). Evaporate in vacuo to a residue. Dissolve the residue in anhydrous dimethylformamide (10 mL) and place under nitrogen atmosphere. Add cesium carbonate (100 mg, 0.3 mmol) in one portion. Stir for 45 minutes at ambient temperature. Add chloromethyl pivalate (42 mg, 0.28 mmol). Stir the resulting mixture at ambient temperature for 18 hours. Quench the reaction with ethyl acetate (3 mL) and water (10 mL). Separate the organic phase and wash with water (7×10 mL), ¼ saturated potassium hydrogen carbonate (10 mL), water (10 mL), and saturated sodium chloride (10 mL). Dry (MgSO$_4$), filter and evaporate in vacuo to yield the title compound.

EXAMPLE 3

4S-[4α, 7α(R*), 12bβ]]-7-[(2-(2-(carbomethoxymethyl)-2-oxoindan)methylamino]-1,2,3,4,6,7,8,12b-octahydro-6-oxopyrido[2,1-a][2]benzazepine-4-carboxylic acid Dissolve 2-carboxyindanlic acid (1.62 g, 10 mmol) in dimethylformamide (5 mL) and add t-butyldimethylsilyl chloride (7.5 g, 50 mmol) and imidazole (6.8 g, 0.1 mol). Stir for 48 hours at room temperature, pour into ethyl ether and water and separate the organic phase. Dry (MgSO$_4$) and evaporate the solvent in vacuo to give 2-(carbo-t-butyldimethylsilyloxy)indan.

Dissolve diisopropylamine (0.88 mL, 6.28 mmol) in tetrahydrofuran (7.5 mL) and place under a nitrogen atmosphere. Cool in an ice bath and add, by dropwise addition, n-butyllithium (3.6 mL of a 1.6M solution in hexanes, 5.75 mmol). Stir for 15 minutes, then cool to 78° C. Add a solution of 2-(carbo-t-butyldimethylsilyloxy)indan (1.39 g, 5.04 mmol) in tetrahydrofuran (5 mL). Stir for 45 minutes then add methyl bromoacetate (949 mg, 6.2 mmol). Stir for 3 hours, add saturated ammonium chloride (6 mL) and warm to room temperature. Partition between ethyl ether (75 mL) and water (10 mL). Dry (Na$_2$SO$_4$), evaporate the solvent in vacuo and purify by silica gel chromatography to give 2-(carbo-t-butyldimethylsilyloxy)-2-(carbomethoxymethyl)indan.

Dissolve 2-(carbo-t-butyldimethylsilyloxy)-2-(carbomethoxymethyl)indan (3.17 g, 9.13 mmol) in tetrahydrofuran (11 mL) and place under an argon atmosphere. Add, by dropwise addition, tetra-n-butylammonium fluoride (11 mL of a 1M solution in tetrahydrofuran, 11 mmol). Stir for 1 hour at room temperature and partition between ethyl ether and water. Separate the organic phase, wash with saturated aqueous sodium chloride, dry (MgSO$_4$), filter and evaporate the solvent in vacuo to give 2-carboxy-2-(carbomethoxymethyl)indan.

Dissolve [4S-[4α, 7α(R*), 12bβ]]-7-(amino)-1,2,3,4,6,7, 8,12b-octahydro-6-oxopyrido[2,1-a][2]benzazepine-4-carboxylic acid, diphenylmethyl ester (150 mg, 0.34 mmol) and EDC (98 mg, 0.50 mmol) in tetrahydrofuran (5 mL). Treat with 2-carboxy-2-(carbomethoxymethyl)indan (100 mg, 0.426 mmol). Stir at room temperature for 15 hours and evaporate the solvent in vacuo. Partition the residue between ethyl acetate (35 mL) and 1N hydrochloric acid (6 ml). Wash the organic phase with saturated sodium hydrogen carbonate (6 mL). Dry (Na$_2$SO$_4$) and evaporate the solvent in vacuo. Purify by silica gel chromatography to give [4S-[4α, 7α(R*), 12bβ]]-7-[(2-(carbomethoxymethyl)-2-oxoindan)-methylamino]-1,2,3,4,6,7,8,12b-octahydro-6-oxopyrido[2, 1-a][2]benzazepine-4-carboxylic acid, diphenylmethyl ester.

Suspend [4S-[4α, 7α(R*), 12bβ]]-7-[(2-carbomethoxymethyl-2-oxoindan)methyl]-1,2,3,4,6,7,8,12b-octahydro-6-oxopyrido[2,1-a][2]benzazepine-4-carboxylic acid, diphenylmethyl ester (3.28 g, 5 mmol) in anhydrous methanol 10 mL) and add 10% palladium/carbon (0.2–0.3 g). Add anhydrous ammonium formate (23 mmol) in a single portion under an argon atmosphere. Stir at room temperature for 3–40 minutes, remove the catalyst by filtration through filter aid and wash with dry methanol (10 mL). Evaporate the solvent in vacuo, extract into ethyl acetate and dry (Na$_2$SO$_4$). Evaporate the solvent in vacuo and purify by silica gel chromatography to give the title compound.

EXAMPLE 4

[4S-[4α, 7α(R*), 12bβ]]-7-[(2-Carbomethoxymethyl-2-oxoindan)methylamino]-1,2,3,4,6,7,8,12b-octahydro-6-oxopyrido[2,1-a][2]benzazepine-4-carboxylic acid, pivaloyloxymethyl ester Dissolve [4S-[4α, 7α(R*), 12bβ]]-7-[(2-carbomethoxymethyl-2-oxoindan)methylammino]-1,2,3,4,6,7,8,12b-octahydro-6-oxopyrido[2,1-a ][2]benzazepine-4-carboxylic acid (137 mg, 0.28 mmol) in methylene chloride (1 mL) and dry over anhydrous MgSO$_4$ (60 mg). Filter and wash with methylene chloride (3×20 mL). Evaporate in vacuo to a residue. Dissolve the residue in anhydrous dimethylformamide (10 mL) and place under nitrogen atmosphere. Add cesium carbonate (100 mg, 0.3 mmol) in one portion. Stir for 45 minutes at ambient temperature. Add chloromethyl pivalate (42 mg, 0.28 mmol). Stir the resulting mixture at ambient temperature for 18 hours. Quench the reaction with ethyl acetate (3 mL) and water (10 mL). Separate the organic phase and wash with water (7×10 mL), ¼ saturated potassium hydrogen carbonate (10 mL), water (10 mL), and saturated sodium chloride (10 mL). Dry (MgSO$_4$), filter and evaporate in vacuo to yield the title compound.

EXAMPLE 5

[4S-[4α, 7α(R*), 12bβ]]-7-[(2-Carboxymethyl-2-oxoindan)-methylamino]-1,2,3,4,6,7,8,12b-octahydro-6-oxopyrido[2,1-a][2]benzazepine-4-carboxylic acid, pivaloyloxymethyl ester Dissolve [4S-[4α, 7α(R*), 12bβ]]-7-[(2-carbomethoxymethyl-2-oxoindan)methylamino]-1,2,3,4,6,7,8,12b-octahydro-6-oxopyrido[2,1-a][2]benzazepine-4-carboxylic acid, pivaloyloxymethyl ester (72 mg, 0.12 mmol) in methanol (3 mL) and 1N aqueous lithium hydroxide (0.50 mL, 0.50 mmol). Stir for 30 minutes under an argon atmosphere at ambient temperature. Reduce in volume to 1.5 mL in vacuo, then add, by dropwise addition, to a rapidly stirring solution of 2N hydrochloric acid (2 mL). Collect the resulting precipitate, wash with water and dry in a vacuum dessicator for 1 hour. Dry at 35° C. overnight to give the title compound.

EXAMPLE 6

[4S-[4α, 7α(R*), 12bβ]]-7-[(2-Pivaloyloxymethylcarboxymethyl-2-oxoindan)methylamino]-1,2,3,4,6,7,8,12b-octahydro-6-oxopyrido[2,1-a][2]benzazepine-4-carboxylic acid Dissolve [4S-[4α, 7α(R*), 12bβ]]-7-[(2-(carbomethoxymethyl)-2-oxoindan)methylamino]-1,2,3,4,6,7,8,12b-octahydro-6-oxopyrido[2,1-a][2]benzazepine-4-carboxylic acid, diphenylmethyl ester (79 mg, 0.12 mmol) in methanol (3 mL) and aqueous 1N lithium hydroxide (0.50 mL, 0.50 mmol). Stir for 30 minutes under an argon atmosphere at ambient temperature. Reduce in volume to 1.5 mL in vacuo, then add, by dropwise addition, to a rapidly stirring solution of 2N hydrochloric acid (2 mL). Collect the resulting precipitate, wash with water and dry in a vacuum dessicator for 1 hour. Dry at 35° C. overnight to give [4S-[4α, 7α(R*), 12bβ]]-7-[(2-(carboxymethyl)-2-oxoindan)methylamino]-1,2,3,4,6,7,8,12b-octahydro-6-oxopyrido[2,1-a][2]benzazepine-4-carboxylic acid, diphenylmethyl ester.

Dissolve [4S-[4α, 7α(R*), 12bβ]]-7-[(2-carboxymethyl-2-oxoindan(methylamino]-1,2,3,4,6,7,8,12b-octahydro-6-oxopyrido[2,1-a ][2]benzazepine-4-carboxylic acid, diphenylmethyl ester (180 mg, 0.28 mmol) in methylene chloride (1 mL) and dry over anhydrous MgSO₄ (60 mg). Filter and wash with methylene chloride (3×20 mL). Evaporate in vacuo to a residue. Dissolve the residue in anhydrous dimethylformamide (10 mL) and place under a nitrogen atmosphere. Add cesium carbonate (100 mg, 0.3 mmol) in one portion. Stir for 45 minutes at ambient temperature. Add chloromethyl pivalate (42 mg, 0.28 mmol). Stir the resulting mixture at ambient temperature for 18 hours. Quench the reaction with ethyl acetate (3 mL) and water (10 mL). Separate the organic phase and wash with water (7×10 mL), ¼ saturated potassium hydrogen carbonate (10 mL), water (10 mL), and saturated sodium chloride (10 mL). Dry (MgSO₄), filter and evaporate in vacuo to give [4S-[4α, 7α(R*), 12bβ]]-7-[(2-pivaloyloxymethylcarboxymethyl-2-oxoindan)methylamino]-1,2,3,4,6,7,8,12b-octahydro-6-oxopyrido[2,1-a][2]benzazepine-4-carboxylic acid, diphenylmethyl ester.

Suspend [4S-[4α, 7α(R*), 12bβ]]-7-[(2-pivaloyloxymethylcarboxymethyl-2-oxoindan)methylamino]-1,2,3,4,6,7,8,12b-octahydro-6-oxopyrido[2,1-a][2]benzazepine-4-carboxylic acid, diphenylmethyl ester (3.78 g, 5 mmol) in anhydrous methanol (10 mL) and add 10% palladium/carbon (0.2–0.3 g). Add anhydrous ammonium formate (23 mmol) in a single portion under an argon atmosphere. Stir at room temperature for 3–40 minutes, remove the catalyst by filtration through filter aid and wash with dry methanol (10 mL). Evaporate the solvent in vacuo, extract into ethyl acetate and dry (Na₂SO₄). Evaporate the solvent in vacuo and purify by silica gel chromatography to give the title compound.

EXAMPLE 7

[4S-[4α, 7α(R*), 12bβ]]-7-[(1-Carboxymethyl-1-oxocyclopentane)methylamino]-1,2,3,4,6,7,8,12b-octahydro-6-oxopyrido[2,1-a][2]benzazepine-4-carboxylic acid Dissolve diisopropylamine (1.4 mL, 10 mmol) in tetrahydrofuran (20 mL) and cool in an ice bath. Add, by dropwise addition, n-butyllithium (5.4 mL of a 1.6M solution in hexanes, 8.6 mmol). Stir for 15 minutes, cool to −78° C. and add a solution of methyl cyclopentanecarboxylate (966 mg, 7.54 mmol) in tetrahydrofuran (10 mL). Stir for 45 minutes then treat with 1,3-dimethyl-3,4,5,6-tetrahydro-2(1H)-pyrimidinone (DMPU) (1.2 mL, 10 mmol). Stir for 5 minutes then add t-butyl bromoacetate (1.46 mL, 9.04 mmol). Stir for 5 hours at −78° C., remove the cold bath and quench with saturated aqueous ammonium chloride (5 mL) after 10 minutes. Partition between water (50 mL) and ethyl acetate (100 mL). Dry (Na₂SO₄) and pass through a plug of silica gel (4:1 hexane/ethyl acetate) to give 1-(carbomethoxy)-1-(carbo-t-butyloxymethyl)cyclopentane.

Dissolve 1-(carbomethoxy)-1-(carbo-t-butyloxymethyl)cyclopentane (1.84 g, 7.59 mmol) in 95% ethanol (50 mL) and water (25 mL). Treat with potassium hydroxide (2.6 g, 46 mmol). Stir at room temperature for 48 hours and evaporate the solvent in vacuo. Partition between water (50 mL) and ethyl ether (150 mL). Acidify the aqueous phase with solid tartaric acid and extract with methylene chloride (125 mL). Wash the organic phase with brine (50 mL), dry (Na₂SO₄) and evaporate the solvent in vacuo to give 1-(carboxy)-1-(carbo-t-butyloxymethyl)cyclopentane as a pale yellow oil (1.23 g, 71%).

Dissolve [4S-[4α, 7α(R*), 12bβ]]-7-(amino)-1,2,3,4,6,7,8,12b-octahydro-6-oxopyrido[2,1-a][2]benzazepine-4-carboxylic acid, diphenylmethyl ester 220 mg, 0.50 mmol, EDC (144 mg, 0.75 mmol) and 1-(carboxy)-1-(carbo-t-butyloxymethyl)cyclopentane (130 mg, 0.57 mmol) in tetrahydrofuran (5 mL). Stir at room temperature for 18 hours and evaporate the solvent in vacuo. Partition the residue between water (3 mL), ethyl acetate (30 mL) and 5% sulfuric acid (20 mL). Separate the organic phase and wash with saturated sodium hydrogen carbonate (15 mL). Back extract the acidic phase with ethyl acetate (20 mL), combine the organic phases and dry (Na₂SO₄). Evaporate the solvent in vacuo and purify by silica gel chromatography (2:1 hexane/ethyl acetate to 3:2 hexane/ethyl acetate) to give [4S-[4α, 7α(R*), 12bβ]]-7-[(1-carbo-t-butyloxymethyl-1-oxocyclopentane)methylamino]-1,2,3,4,6,7,8,12b-octahydro-6-oxopyrido[2,1-a][2]benzazepine-4-carboxylic acid, diphenylmethyl ester as a white foam (170 mg, 52%).

Dissolve [4S-[4α, 7α(R*), 12bβ]]-7-[(1-carbo-t-butyloxymethyl-1-oxocyclopentane)methylamino]-1,2,3,4,6,7,8,12b -octahydro-6-oxopyrido[2,1-a][2]benzazepine-4-carboxylic acid, diphenylmethyl ester (170 mg, 0.261 mmol) in methylene chloride (3 mL) and treat with anisole (0.28 mL, 2.6 mmol). Cool in an ice-methanol bath and add trifluoroacetic acid (0.8 mL, 1 mmol) and stir for 18 hours. Partition between ethyl acetate (75 mL) and brine (2×20 mL). Separate the organic phase and wash with brine (15 mL). Dry (Na₂SO₄), evaporate the solvent in vacuo and purify by silica gel chromatography (2:1 hexane/ethyl acetate) to give the title compound as a white powder.

EXAMPLE 8

[4S-[4α, 7α(R*), 12bβ]]-7-[(5-Carboxymethyl-5-oxo-cyclopentimidazole)methylamino]-3,4,6,7,8,12b-hexahydro-6-oxo-1H-[1,4]-oxazino[3,4-a][2]benzazepine-4-carboxylic acid Scheme D, step a: N-[2-(1,3-Dihydro-1,3-dioxo-2H-isoindol-2-yl)-1-oxo-3-phenylpropyl]-L-serine, methyl ester Slurry N-phthaloyl-(S)-phenylalanine (90 g, 0.3 mol) in methylene chloride (450 mL) and add, by dropwise addition, oxalyl chloride (54 mL, 0.62 mol). Place under a dry atmosphere (CaSO₄ tube) and treat with dimethylformamide (10 μL). Stir for 5 hours, filter and concentrate in vacuo to give N-phthaloyl-(S)-phenylalanine, acid chloride as an off white amorphous solid.

Dissolve serine methyl ester hydrochloride (56 g, 0.36 mol) in tetrahydrofuran (300 mL) then cool to 0° C. and add 4-methylmorpholine (88 mL, 0.8 mol). Add, by dropwise addition, a solution of the N-phthaloyl-(S)-phenylalanine, acid chloride in tetrahydrofuran (200 mL). Allow to warm to room temperature and stir for 3 hours. Filter and concentrate the filtrate in vacuo. Dissolve the residue in ethyl acetate and separate the organic phase. Wash with water then saturated sodium chloride and dry (MgSO$_4$). Evaporate the solvent in vacuo to give an oil. Purify by silica gel chromatography (gradient 50% ethyl acetate/hexane to ethyl acetate) to give the title compound (80.8 g, 67%) mp 129°–132° C.

Scheme D, step b: N-[2-(1,3-Dihydro-1,3-dioxo-2H-isoindol-2-yl)-1-oxo-3-phenylpropyl]-O-2-propenyl-L-serine, methyl ester Dissolve N-[2-(1,3-dihydro-1,3-dioxo-2H-isoindol-2-yl)-1-oxo-3-phenylpropyl]-L-serine, methyl ester (25 g, 63 mmol) in methylene chloride/cyclohexane (1:1, 600 mL). Add allyl trichloroacetimidate (26 g, 128 mmol) and trifluoromethanesulfonic acid (5 mL), 56.6 mmol). Stir at room temperature under a nitrogen atmosphere for 5 hours and dilute with methylene chloride. Wash with saturated aqueous sodium hydrogen carbonated water, dry (MgSO$_4$) and evaporate the solvent in vacuo. Purify by silica gel chromatography (gradient 20% ethyl acetate/hexane to 35% ethyl acetate/hexane) to give the title compound; mp 95°–97° C.

Scheme D, step c: [S-(R*, R*)]-N-[2-(1,3-Dihydro-1,3-dioxo-2H-isoindol-2-yl)-1-oxo-3-phenylpropyl]-3,4-dihydro-2H-1,4-oxazine-3-carboxylic acid, methyl ester Dissolve N-[2-(1,3-dihydro-1,3-dioxo-2H-isoindol-2-yl)-1-oxo-3-phenylpropyl]-O-2-propenyl-L-serine, methyl ester (13 g, 29.8 mmol) in methylene chloride/methanol (10:1, 220 mL). Cool to −78° C. and sparge with a mixture of ozone/oxygen for approximately 10 minutes until a blue color persists. Sparge with nitrogen for 10 minutes at −78° C. to remove excess ozone. Treat with methyl sulfide (60 mL, 0.82 mol) and allow to warm no room temperature. Stir at room temperature for 2.5 hours, evaporate the solvent in vacuo and dissolve the residue in ethyl acetate (200 mL). Wash with water, saturated sodium chloride, dry (MgSO$_4$) and evaporate the solvent in vacuo to give the intermediate N-[2-(1,3-dihydro-1,3-dioxo-2H-isoindol-2-yl)-1-oxo-3-phenylpropyl]-O-2-oxoethyl-L-serine, methyl ester as a foam (13.6 g).

Dissolve N-[2-(1,3-dihydro-1,3-dioxo-2H-isoindol-2-yl)-1-oxo-3-phenylpropyl]-O-2-oxoethyl-L-serine, methyl ester (13.6 g) in methylene chloride/trifluoroacetic acid (10:1/330 mL). Stir at room temperature for 2.5 hours and evaporate the solvent in vacuo. Purify by silica gel chromatography (35% ethyl acetate/hexane) and recrystallize (ethyl acetate/hexane) to give the title compound (8.52 g, 68%); mp 70°–72° C.

Scheme D, step d: [4S-[4α, 7α(R*), 12bβ]]-7-[(1,3-Dihydro-1,3-dioxo-2H-isoindol-2-yl)]-3,4,6,7,8,12b-hexahydro-6-oxo-1H-[1,4]-oxazino[3,4-a][2]benzazepine-4-carboxylic acid, diphenylmethyl ester Dissolve [S-(R*, R*)]-N-[2-(1,3-dihydro-1,3-dioxo-2H-isoindol-2-yl)-1-oxo-3-phenylpropyl]-3,4-dihydro-2H-1,4-oxazine-3-carboxylic acid, methyl ester (2.5 g, 5.9 mmol) in methylene chloride (5 mL) and add, by dropwise addition, to a previously prepared solution of trifluoromethanesulfonic acid (4.0 mL, 45 mmol) and trifluoroacetic anhydride (1.0 mL, 7.1 mmol). Place under a nitrogen atmosphere and stir at room temperature for 123 hours. Pour into a separatory funnel containing ice (200 g) and ethyl acetate (200 mL). Separate the organic phase, wash with water (3×200 mL) and saturated aqueous sodium chloride (100 mL). Extract the organic phase with 10% wt. potassium hydrogen carbonate (4×40 mL) and water (40 mL). Layer the combined basic aqueous phases with ethyl acetate (100 mL) and cool in an ice bath. Add, by dropwise addition, 6N hydrochloric acid to adjust the pH to 1 while maintaining the temperature at 5°–10° C. Separate the organic phase and extract the aqueous phase with ethyl acetate (3×200 mL), wash with saturated sodium chloride and dry (MgSO$_4$). Evaporate the solvent in vacuo and dry the residue under high vacuum at 56° C. for 24 hours to give the intermediate [4S-[4α, 7α(R*), 12bβ]]-7-[(1,3-dihydro-1,3-dioxo-2H-isoindol-2-yl)]-3,4,6,7,8,12b-hexahydro-6-oxo-1H-[1,4]-oxazino[3,4-a][2]benzazepine-4-carboxylic acid (1.75 g, 73%). Dissolve [4S-[4α, 7α(R*), 12bβ]]-7-[(1,3-dihydro-1,3-dioxo-2H-isoindol-2-yl)]-3,4,6,7,8,12b-hexahydro-6-oxo-1H-[1,4]-oxazino[3,4-a][2]benzazepine-4-carboxylic acid (500 mg, 1.23 mmol) in methylene chloride (12 mL) and treat with diphenyldiazomethane (360 mg, 1.86 mmol). Stir for 5.5 hours and evaporate the solvent in vacuo. Purify by silica gel chromatography (gradient 20% ethyl acetate/hexane to 35% ethyl acetate/hexane) to give the title compound (563 mg, 80%); mp 178°–181° C. (isopropanol).

Scheme D, step e: [4S-[4α, 7α(R*), 12bβ]]-7-(Amino)-3,4,6,7,8,12b-hexahydro-6-oxo-1H-[1,4]-oxazino[3,4-a][2]benzazepine-4-carboxylic acid, diphenylmethyl ester Dissolve [4S-[4α, 7α(R*), 12bβ]]-7-[(1,3-dioxo-2H-isoindol-2-yl)]-3,4,6,7,8,12b-hexahydro-6-oxo-1H-[1,4]-oxazino[3,4-a][2]benzazepine-4-carboxylic acid, diphenylmethyl ester (296 mg, 0.517 mmol) in methanol (5 mL) and treat with hydrazine monohydrate (1.1 mL of a 1M solution in methanol, 1.1 mmol). Stir at room temperature for 44 hours, evaporate the solvent in vacuo and slurry the residue in methylene chloride (10 mL). Filter and evaporate the solvent in vacuo to give the title compound (218 mg, 95%).

Scheme A: [4S-[4α, 7α(R*), 12bβ]]-7-[(5-Carboxymethyl-5-oxo-cyclopentimidazole)methylamino]-3,4,6,7,8,12b-hexahydro-6-oxo-1H-[1,4]-oxazino[3,4-a][2]benzazepine-4-carboxylic acid Dissolve 4,5-imidazoledicarboxylic acid (31.2 g, 0.2 mol) in ethanol (500 mL) and treat with concentrated sulfuric acid (0.5 mL). Heat to 60° C. for 16 hours, cool and reduce the solvent by 50% in vacuo. Dilute with ethyl ether (500 mL), wash with saturated sodium hydrogen carbonate, then brine. Dry (MgSO$_4$) and evaporate the solvent in vacuo to give 4,5-(dicarboethoxy)imidazole.

Dissolve 4,5-(dicarboethoxy)imidazole (1.06 g, 5 mmol) and triethylamine (1.5 mL, 7.5 mmol) in 50/50 dioxane water (25 mL). Add [2-(tert-butyloxycarbonyloxyimino)-2-phenylacetonitrile](1.36 g, 5.5 mmol) and stir at room temperature for 2 hours. Add water (7.5 mL) and ethyl acetate (10 mL), separate the aqueous phase and wash with ethyl acetate (10 mL). Combine the organic phases, dry (MgSO$_4$) and evaporate the solvent in vacuo. Purify the residue by silica gel chromatography to give N-(carbo-t-butyloxy)-4,5-(dicarboethoxy)imidazole.

Dissolve N-(carbo-t-butyloxy)-4,5-(dicarboethoxy)imidazole (3.12 g, 10 mmol) in anhydrous tetrahydrofuran (30 mL) and cool to −20° C. Treat with lithium borohydride (7 mL of a 2N solution) and stir under a nitrogen atmosphere for several days. Carefully add water and partition between ethyl acetate and 5% hydrochloric acid. Separate the organic phase, wash with brine and dry (MgSO$_4$). Evaporate the solvent in vacuo and purify by silica gel chromatography to give N-(carbo-t-butyloxy)-4,5-(dihydroxymethyl)imidazole.

Dissolve N-bromosuccinimide (1.78 g, 0.01 mol) in tetrahydrofuran (60 mL) and add a solution of triphenyl phosphine (2.62 g, 0.01 mol) in tetrahydrofuran. Add a solution o f N-(carbo-t-butyloxy)-4,5-(dihydroxymethyl)imidazole (1.14 g, 5 mmol) in tetrahydrofuran (25 mL) and stir until most of the solid goes into solution. Evaporate the solvent in vacuo and partition the residue between water and ethyl ether. Separate the organic phase and wash with water. Dry ($Na_2SO_4$) and evaporate the solvent in vacuo. Purify by silica gel chromatography to give N-(carbo-t-butyloxy)-4,5-(dibromomethyl)imidazole.

Dissolve diethylmalonate (15.2 mL, 0.100 mol) in tetrahydrofuran (800 mL). Cool in an ice bath and treat with sodium hydride (3.0 g, 0.10 mol, 80% in mineral oil). Stir until solution attained and add N-(carbo-t-butyloxy)-4,5-(dibromomethyl)imidazole (35.4 g, 0.100 mol). Stir for 30 minutes then add additional sodium hydride (3.0 g, 0.10 mol). Stir at room temperature for 20 hours, filter through filter aid and evaporate the solvent in vacuo. Purify by silica gel chromatography to give 5,5-(dicarboethoxy)-1-(carbo-t-butyloxy)-cyclopentimidazole.

Dissolve 5,5-(dicarboethoxy)-1-(carbo-t-butyloxy)-cyclopentimidazole (21.3 g, 60.6 mmol) in dimethylsulfoxide (140ml). Add water (14 mL) and lithium chloride (7.0 g, 0.16 mol). Heat at reflux for 4 hours, cool and partition between water (150 mL) and methylene chloride (2×150 mL). Wash the organic phase with water (150 mL), dry ($Mg_sO_4$) and pass through a silica gel plug to give 5-(carboethoxy)-1-(carbo-t-butyloxy)-cyclopentimidazole.

Dissolve 5-(carboethoxy)-1-(carbo-t-butyloxy)cyclopentimidazole (9.5 g, 34.1 mmol) in ethanol (95%, 150 mL) and water (75 mL). Add potassium hydroxide (9.5 g, 0.17 mol) and stir at room temperature for 1 hour. Partition between water (150 mL) and ethyl ether (2×150 mL). Acidify the aqueous phase with hydrochloric acid to pH 1. Extract with methylene chloride (2×150 mL), dry ($Na_2SO_4$) and evaporate the solvent in vacuo to give 5-(carboxy)-1-(carbo-t-butyloxy)-cyclopentimidazole.

Dissolve 5-(carboxy)-1-(carbo-t-butyloxy)-cyclopentimidazole (5.9 g, 23.5 mmol) in methanol (60 mL) and treat with dimethoxypropane (5.8 mL, 47 mmol) and sulfuric acid (0.8 mL). Stir at room temperature for 1 day. Evaporate the solvent in vacuo, dilute with methylene chloride (75 mL) and wash with saturated sodium hydrogen carbonate (35 mL). Extract the aqueous phase with methylene chloride (30 mL), wash combined organics with brine (30 mL) and dry ($Na_2SO_4$). Evaporate the solvent in vacuo and pass through a plug of silica gel to give 5-(carbomethoxy)-1-(carbo-t-butyloxy)cyclopentimidazole.

Dissolve diisopropylamine (3.5 mL, 25 mmol) in tetrahydrofuran (30 mL). Add n-butyllithium (14 mL of a 1.6M solution in hexane, 22.4 mmol). Stir for 15 minutes and cool to −78° C. Add, by dropwise addition, 5-(carbomethoxy)-1-(carbo-t-butyloxy)-cyclopentimidazole (5.32 g, 20 mmol) and stir for 30 minutes. Add t-butyl bromoacetate (4.0 mL, 25 mmol) and gradually warm to room temperature overnight. Quench the solution with ammonium chloride solution (10 mL) and partition between water (25 mL) and ethyl ether (50 mL). Separate the organic phase, dry ($MgSO_4$) and evaporate the solvent in vacuo. Purify by silica gel chromatography to give 5-(carbomethoxy)-1-(carbo-t-butyloxy)-5-(carbo-t-butyloxymethyl)-cyclopentimidazole.

Dissolve 5-(carbomethoxy)-1-(carbo-t-butyloxy)-5-(carbo-t-butyloxymethyl)-cyclopentimidazole (3.48 g, 9.17 mmol) in ethanol (95%, 60 mL) and water (30 mL). Treat with potassium hydroxide (2.94 g, 52 mmol). Stir at room temperature for 3 hours. Add water (75 mL) and extract with ethyl ether (2×50 mL). Extract the combined ethereal phases with water (75 mL) and acidify the combined aqueous phases with aqueous 1M tartaric acid (pH 2–3). Extract with ethyl acetate (2×125 mL), dry ($Na_2SO_4$) and evaporate the solvent in vacuo. Take the residue up in methylene chloride and filter to give 5-(carboxy)-1-(carbo-t-butyloxy)-5-(carbo-t-butyloxymethyl)-cyclopentimidazole.

Dissolve [4S-[4α, 7α(R*), 12bβ]]-7-(amino)-3,4,6,7,8,12b-hexahydro-6-oxo-1H-[1,4]-oxazino[3,4-a][2]benzazepine-4-carboxylic acid, diphenylmethyl ester (200 mg, 0.454 mmol) and EDC (130 mg, 0.68 mmol) in tetrahydrofuran (5 mL). Treat with 5-(carboxy)-1-(carbo-t-butyloxy)-5-(carbo-t-butyloxymethyl)-cyclopentimidazole (166 mg, 0.454 mmol). Stir at room temperature for 20 hours and evaporate the solvent in vacuo. Dissolve the residue in ethyl acetate (50 mL) and wash with 5% sulfuric acid (15 ml) then saturated sodium hydrogen carbonate (15 mL). Dry ($Na_2SO_4$) and evaporate the solvent in vacuo. Purify by silica gel chromatography to give [4S-[4α, 7α(R*), 12bβ]]-7-[(5-(carbo-t-butyloxymethyl)-5-oxo-1-(carbo-t-butyloxy)-cyclopentimidazole)methylamino]-3,4,6,7,8,12b-hexahydro-6-oxo-1H-[1,4]-oxazino[3,4-a][2]benzazepine-4-carboxylic acid, diphenylmethyl ester.

Dissolve [4S-[4α, 7α(R*), 12bβ]]-7-[(5-(carbo-t-butyloxymethyl)-5-oxo-1-(carbo-t-butyloxy)-cyclopentimidazole)methylamino]-3,4,6,7,8,12b-hexahydro-6-oxo-1H-[1,4-oxazine[3,4-a][2]benzazepine-4-carboxylic acid, diphenylmethyl ester (129 mg, 0.163 mmol) in methylene chloride (3 mL) and treat with anisole (0.19 mL, 1.7 mmol). Cool in an ice-methanol bath and add trifluoroacetic acid (0.8 mL, 10 mmol) and stir for 2.5 hours at 0° C. Partition between ethyl acetate (25 mL) and brine (15 mL). Separate the organic phase and wash with brine (15 mL). Dry ($Na_2SO_4$), evaporate the solvent in vacuo and purify by silica gel chromatography to give the title compound.

EXAMPLE 9

Preparation of [4S-[4α, 7α(R*), 12bβ]]-7-[(5-Carboxymethyl-5-oxo-4,5,6-trihydro-cyclopenta[c]furan)methylamino]-3,4,6,7,8,12b-hexahydro-6-oxo-1H-[1,4]-thiazino[3,4-a][2]benzazepine-4-carboxylic acid Dissolve 3,4-(dicarboethoxy)furan (2.12 g, 10mmol) in anhydrous tetrahydrofuran (30 mL) and cool to −20° C. Treat with lithium borohydride (7 mL of a 2N solution). and stir under a nitrogen atmosphere for several days. Carefully add water and partition between ethyl acetate and 5% hydrochloric acid. Separate the organic phase, wash with brine and dry ($MgSO_4$). Evaporate the solvent in vacuo and purify by silica gel chromatography to give 3,4-(dihydroxymethyl)furan.

Dissolve 3,4-(dihydroxymethyl) furan (11.9 g, 0. 093 mol) in 2,4,6-collidine (12.4 g) and add a solution of lithium bromide (7.9 g, 91 mmol) in dimethylformamide (80 mL). Cool to −50° C. and place under a nitrogen atmosphere. Add methanesulfonyl chloride (11.8 g) at a rate which keeps the temperature under 0° C. Stir at 0° C. for 2 hours and pour onto ice water. Extract with ethyl ether, dry ($MgSO_4$), evaporate the solvent in vacuo and purify by silica gel chromatography to give 3,4-(dibromomethyl)furan.

Dissolve diethylmalonate (15.2 mL, 0.100 mol) in tetrahydrofuran (800 mL). Cool in an ice bath and treat with sodium hydride (3.0 g, 0.10mol, 80% in mineral oil). Stir until solution attained and add 3,4-(dibromomethyl)furan (23.8 g, 0.100 mol). Stir for 30 minutes then add additional sodium hydride (3.0 g, 0.10mol). Stir at room temperature for 20 hours, filter through filter aid and evaporate the solvent in vacuo. Purify by silica gel chromatography to give 5,5-(dicarboethoxy)-2,4,5,6-tetrahydrocyclopenta [c]furan.

Dissolve 5,5-(dicarboethoxy)-2,4,5,6-tetrahydro-cyclopenta[c]furan (15.3 g, 60.6 mmol) in dimethylsulfoxide (140 ml). Add water (14 mL) and lithium chloride (7.0 g, 0.16 mol). Heat at reflux for 4 hours, cool and partition between water (150 mL) and methylene chloride (2×150 mL). Wash the organic phase with water (150 mL), dry ($Mg_sO_4$) and pass through a silica gel plug to g ire 5-(carboethoxy)-2,4, 5,6-tetrahydro-cyclopenta[c]furan.

Dissolve 5-(carboethoxy)-2,4,5,6-tetrahydro-cyclopenta [c]furan (6.2 g, 34.1 mmol) in ethanol (95%, 150 mL) and water (75 mL). Add potassium hydroxide (9.5 g, 0.17 mol) and stir at room temperature for 1 hour. Partition between water (150 mL) and ethyl ether (2×150 mL). Acidify the aqueous phase with hydrochloric acid to pH 1. Extract with methylene chloride (2×150 mL), dry ($Na_2SO_4$) and evaporate the solvent in vacuo to give 5-(carboxy)-2,4,5,6-tetrahydro-cyclopenta[c]furan.

Dissolve 5-(carboxy)-2,4,5,6-tetrahydro-cyclopenta[c]furan (3.6 g, 23.5 mmol) in methanol (60 mL) and treat with dimethoxypropane (5.8 mL, 47 mmol) and sulfuric acid (0.8 mL). Stir at room temperature for 1 day. Evaporate the solvent in vacuo, dilute with methylene chloride (75 mL) and wash with saturated sodium hydrogen carbonate (35 mL). Extract the aqueous phase with methylene chloride (30 mL), wash combined organics with brine (30 mL) and dry ($Na_2SO_4$). Evaporate the solvent in vacuo and pass through a plug of silica gel to give 5-(carbomethoxy)-2,4,5,6-tetrahydro-cyclopenta[c]furan.

Dissolve diisopropylamine (3.5 mL, 25 mmol) in tetrahydrofuran (30 mL) Add n-butyllithium (14 mL of a 1.6M solution in hexane 22.4 mmol). Stir for 15 minutes and cool to –78° C. Add, by dropwise addition, 5-(carbomethoxy)-2,4,5,6-tetrahydro-cyclopenta[c]furan (3.32 g, 20 mmol) and stir for 30 minutes. Add t-butyl bromoacetate (4.0 mL, 25 mmol) and gradually warm to room temperature overnight. Quench the solution with ammonium chloride solution (10 mL) and partition between water (25 mL) and ethyl ether (50 mL). Separate the organic phase, dry ($MgSO_4$) and evaporate the solvent in vacuo. Purify by silica gel chromatography to give 5-(carbomethoxy)-5-(carbo-t-butyloxymethyl)-2,4,5,6-tetrahydro-cyclopenta[c]furan.

Dissolve 5-(carbomethoxy)-5-(carbo-t-butyloxymethyl)-2,4,5,6-tetrahydro-cyclopenta[c]furan (2.6 g, 9.17 mmol) in ethanol (95%, 60 mL) and water (30 mL). Treat with potassium hydroxide (2.94 g, 52 mmol). Stir at room temperature for 3 hours. Add water (75 mL) and extract with ethyl ether (2×50 mL). Extract the combined ethereal phases with water (75 mL) and acidify the combined aqueous phases with aqueous 1M tartaric acid (pH 2–3). Extract with ethyl acetate (2×125 mL), dry ($Na_2SO_4$) and evaporate the solvent in vacuo. Take the residue up in methylene chloride and filter to give 5-(carboxy)-5-(carbo-t-butyloxymethyl)-2, 4,5,6-tetrahydro-cyclopenta[c]furan.

Dissolve [4S-[4α, 7α(R*), 12bβ]]-7-(amino)-3,4,6,7,8, 12b-hexahydro-6-oxo-1H-[1,4]-thiazino[3,4-a][2]benzazepine-4-carboxylic acid, diphenyl methyl ester (208 mg, 0.454 mmol) and EDC (130 mg, 0.68 mmol) in tetrahydrofuran (5 mL). Treat with 5-(carboxy)-5-(carbo-t-butyloxymethyl)-2,4,5,6-tetrahydro-cyclopenta[c]furan (121 mg, 0.454 mmol). Stir at room temperature for 20 hours and evaporate the solvent in vacuo. Dissolve the residue in ethyl acetate (50 mL) and wash with 5% sulfuric acid (15 ml) then saturated sodium hydrogen carbonate (15 mL). Dry ($Na_2SO_4$) and evaporate the solvent in vacuo. Purify by silica gel chromatography to give [4S-[4α, 7αC(R*), 12bβ] ]-7-[(5-carbo-t-butyloxymethyl-5-oxo-2,4,5,6-tetrahydro-cyclopenta [c]furan)methylamino ]-3,4,6,7,8,12b-hexahydro-6-oxo-1H-[1,4 ]-thiazino[3,4-a ][2]benzazepine-4-carboxylic acid, diphenylmethyl ester.

Dissolve [4S- [4α, 7α(R*), 12bβ]]-7-[(5-carbo-t-butyloxymethyl-5-oxo-2,4,5,6-tetrahydro-cyclopenta[c]furan)-methylamino]-3,4,6,7,8,12b-hexahydro-6-oxo-1H-[1,4]-thiazino[3,4-a][2]benzazepine-4-carboxylic acid, diphenylmethyl ester (115 mg, 0.163 mmol) in methylene chloride (3 mL) and treat with anisole (0.19 mL, 1.7 mmol). Cool in an ice-methanol bath and add trifluoroacetic acid (0.8 mL, 10 mmol) and stir for 2.5 hours at 0° C. Partition between ethyl acetate (25 mL) and brine (15 mL). Separate the organic phase and wash with brine (15 mL). Dry ($Na_2SO_4$), evaporate the solvent in vacuo and purify by silica gel chromatography to give the title compound.

EXAMPLE 10

Preparation of [4S-[4α, 7α(R*), 12bβ]]-7-[(5-Carboxymethyl-5-oxo-4,5,6-trihydro-cyclopenta [c]thiophene)methylamino ]-3,4,6,7,8,12b-hexahydro-6-oxo-1H- [1,4]-thiazino [3,4-a][2]benzazepine-4-carboxylic acid Dissolve 3,4-(dicarboethoxy)thiophene (2.28 g, 10 mmol) in anhydrous tetrahydrofuran (30 mL) and cool to –20° C. Treat with lithium borohydride (7 mL of a 2N solution) and stir under a nitrogen atmosphere for several days. Carefully add water and partition between ethyl acetate and 5% hydrochloric acid. Separate the organic phase, wash with brine and dry ($MgSO_4$). Evaporate the solvent in vacuo and purify by silica gel chromatography to give 3,4-(dihydroxymethyl)thiophene.

Dissolve 3,4-(dihydroxymethyl)thiophene (13.4 g, 0.093 mol) 2,4,6-collidine (12.4 g) and add a solution of lithium bromide (7.9 g, 91 mmol) in dimethylformamide (80 mL). Cool to –50° C. and place under a nitrogen atmosphere. Add methanesulfonyl chloride (11.8 g) at a rate which keeps the temperature under 0° C. Stir at 0° C. for 2 hours and pour onto ice water. Extract with ethyl ether, dry ($MgSO_4$), evaporate the solvent in vacuo and purify by silica gel chromatography to give 3,4-(dibromomethyl)thiophene.

Dissolve diethylmalonate (15.2 mL, 0.100 mol) in tetrahydrofuran (800 mL). Cool in an ice bath and treat with sodium hydride (3.0 g, 0.10 mol, 80% in mineral oil). Stir until solution attained and add 3,4-(dibromomethyl)thiophene (25.4 g, 0.100 mol). Stir for 30 minutes then add additional sodium hydride (3.0 g, 0.10 mol). Stir at room temperature for 20 hours, filter through filter aid and evaporate the solvent in vacuo. Purify by silica gel chromatography to give 5,5-(dicarboethoxy)-2,4,5,6-tetrahydrocyclopenta[c]thiophene.

Dissolve 5,5-(dicarboethoxy)-2,4,5,6-tetrahydro-cyclopenta[c]thiophene (16.2 g, 60.6 mmol) in dimethylsulfoxide (140 ml). Add water (14 mL) and lithium chloride (7.0 g, 0.16 mol). Heat at reflux for 4 hours, cool and partition between water (150 mL) and methylene chloride (2×150 mL). Wash the organic phase with water (150 mL), dry ($Mg_sO_4$) and pass through a silica gel plug to give 5-(carboethoxy)-2,4,5,6-tetrahydro-cyclopenta[c]thiophene.

Dissolve 5-(carboethoxy)-2,4,5,6-tetrahydro-cyclopenta [c]thiophene (6.68 g, 34.1 mmol) in ethanol (95%, 150 mL) and water (75 mL). Add potassium hydroxide (9.5 g, 0.17 mol) and stir at room temperature for 1 hour. Partition between water (150 mL) and ethyl ether (2×150 mL). Acidify the aqueous phase with hydrochloric acid to pH 1. Extract with methylene chloride (2×150 mL), dry ($Na_2SO_4$) and evaporate the solvent in vacuo to give 5-(carboxy)-2,4, 5,6-tetrahydro-cyclopenta[c]thiophene.

Dissolve 5-(carboxy)-2,4,5,6-tetrahydro-cyclopenta[c] thiophene (3.95 g, 23.5 mmol) in methanol (60 mL) and treat with dimethoxypropane (5.8 mL, 47 mmol) and sulfuric acid (0.8 mL). Stir at room temperature for 6 days. Evaporate the solvent in vacuo, dilute with methylene chloride (75 mL) and wash with saturated sodium hydrogen carbonate (35 mL). Extract the aqueous phase with methylene chloride (30 mL), wash combined organics with brine (30 mL) and dry ($Na_2SO_4$). Evaporate the solvent in vacuo and pass through a plug of silica gel to give 5-(carbomethoxy)-2,4,5,6-tetrahydro-cyclopenta[c]thiophene.

Dissolve diisopropylamine (3.5 mL, 25 mmol) in tetrahydrofuran (30 mL). Add n-butyllithium (14 mL of a 1.6M solution in hexane, 22.4 mmol). Stir for 15 minutes and cool to −78° C. Add, by dropwise addition, 5-(carbomethoxy)-2,4,5,6-tetrahydro-cyclopenta[c]thiophene (3.64, 20 mmol) and stir for 30 minutes. Add t-butyl bromoacetate (4.0 mL, 25 mmol) and gradually warm to room temperature overnight. Quench the solution with ammonium chloride solution (10 mL) and partition between water (25 mL) and ethyl ether (50 mL). Separate the organic phase, dry ($MgSO_4$) and evaporate the solvent in vacuo. Purify by silica gel chromatography to give 5-(carbomethoxy)-5-(carbo-t-butyloxymethyl)-2,4,5,6-tetrahydro-cyclopenta[c]thiophene.

Dissolve 5-(carbomethoxy)-5-(carbo-t-butyloxymethyl)-2,4,5,6-tetrahydro-cyclopenta[c]thiophene (2.7 g, 9.17 mmol) in ethanol (95%, 60 mL) and water (30 mL). Treat with potassium hydroxide (2.94 g, 52 mmol). Stir at room temperature for 3 hours. Add water (75 mL) and extract with ethyl ether (2×50 mL). Extract the combined ethereal phases with water (75 mL) and acidify the combined aqueous phases with aqueous 1M tartaric acid (pH 2–3). Extract with ethyl acetate (2×125 mL), dry ($Na_2SO_4$) and evaporate the solvent in vacuo. Take the residue up in methylene chloride and filter to give 5-(carboxy)-5-(carbo-t-butyloxymethyl)-2,4,5,6-tetrahydro-cyclopenta[c]thiophene.

Dissolve [4S-[4α, 7α(R*), 12bβ]]-7-(amino)-3,4,6,7,8,12b-hexahydro-6-oxo-1H-[1,4]-thiazino[3,4-a][2]benzazepine-4-carboxylic acid, diphenylmethyl ester (208 mg, 0.454 mmol) and EDC (130 mg, 0.68 mmol) in tetrahydrofuran (5 mL). Treat with 5-(carboxy)-5-(carbo-t-butyloxymethyl)-2,4,5,6-tetrahydro-cyclopenta[c]thiophene (128 mg, 0.454 mmol). Stir at room temperature for 20 hours and evaporate the solvent in vacuo. Dissolve the residue in ethyl acetate (50 mL) and wash with 5% sulfuric acid (15 ml) then saturated sodium hydrogen carbonate (15 mL). Dry ($Na_2SO_4$) and evaporate the solvent in vacuo. Purify by silica gel chromatography to give [4S-[4α, 7α(R*), 12bβ]]-7-[(5-(carbo-t-butyloxymethyl)-5-oxo-2,4,5,6-tetrahydrocyclopenta[c]thiophene)methylamino]-3,4,6,7,8,12b-hexahydro-6-oxo-1H-[1,4]-thiazino[3,4a-][2]benzazepine-4-carboxylic acid, diphenylmethyl ester.

Dissolve [4S-[4α, 7α(R*), 12bβ]]-7-[(5-(carbo-t-butyloxymethyl)-5-oxo-2,4,5,6-tetrahydro-cyclopenta[c]thiophene)methylamino]-3,4,6,7,8,12b-hexahydro-6-oxo-1H-[1,4]-thiazino[3,4-a][2]benzazepine-4-carboxylic acid, diphenylmethyl ester (118 mg, 0.163 mmol) in methylene chloride (3 mL) and treat with anisole (0.19 mL, 1.7 mmol). Cool in an ice-methanol bath and add trifluoroacetic acid (0.8 mL, 10 mmol) and stir for 2.5 hours at 0° C. Partition between ethyl acetate (25 mL) and brine (15 mL). Separate the organic phase and wash with brine (15 mL). Dry ($Na_2SO_4$), evaporate the solvent in vacuo and purify by silica gel chromatography to give the title compound.

EXAMPLE 11

Preparation of [4S-[4α, 7α(R*), 12bβ]]-7-[(5-Carboxymethyl-5-oxo-2,4,5,6-tetrahydro-cyclopenta[c])pyrrole)methylamino]-3,4,6,7,8,12b-hexahydro-6-oxo-1H- [1,4]-azazino[3,4-a][2]benzazepine-4-carboxylic acid Scheme E, step a: N-[2-(1,3-Dihydro-1,3-dioxo-2H-isoindol-2-yl)-1-oxo-3-phenylpropyl]-(S)-3-[(trifluoroacetyl-2-propenyl)amino]-2-amino-propionic acid, methyl ester Dissolve $N^\alpha$-(carbobenzyloxy)-β-(amino)-L-alanine (47.6 g, 0.2 mol) in methanol (500 mL) and treat with concentrated sulfuric acid (0.5 mL). Heat to 60° C. for 16 hours, cool and reduce the solvent by 50% in vacuo. Dilute with ethyl ether (500 mL), wash with saturated sodium hydrogen carbonate, then brine. Dry ($MgSO_4$) and evaporate the solvent in vacuo to give $N^\alpha$-(carbobenzyloxy)-β-(amino)-L-alanine, methyl ester.

Dissolve $N^\alpha$-(carbobenzyloxy)-β-(amino)-L-alanine, methyl ester (15.9 g, 63mmol) in methylene chloride/cyclohexane (1:1, 600 mL). Add allyl trichloroacetimidate (26 g, 128 mmol) and trifluoromethanesulfonic acid (5 mL), 56.6 mmol). Stir at room temperature under a nitrogen atmosphere for 5 hours and dilute with methylene chloride. Wash with saturated aqueous sodium hydrogen carbonate, water, dry ($MgSO_4$) and evaporate the solvent in vacuo. Purify by silica gel chromatography to give $N^\alpha$-(carbobenzyloxy)-β-(allylamino)-L-alanine, methyl ester.

Dissolve $N^\alpha$-(carbobenzyloxy)-β-(allylamino)-L-alanine, methyl ester (663 mg, 2.27 mmol) in anhydrous tetrahydrofuran (15 mL). Treat with pyridine (183 μL, 2.27 mmol) followed by trifluoroacetic anhydride (321 μL, 2.27 mmol) and stir at room temperature overnight. Partition between ethyl ether and water. Separate the organic phase, dry ($MgSO_4$) and evaporate the solvent in vacuo. Purify by silica gel chromatography to give $N^\alpha$-(carbobenzyloxy)-β-(trifluoroacetyl-allylamino)-L-alanine, methyl ester.

Place boron tribromide (215 mg, 0.86 mmol) in a flask and cool to 0° C. Cautiously add trifluoroacetic acid (5 mL) with stirring. Evaporate the solvent to give boron tris(trifluoroacetate).

Dissolve boron tris(trifluoroacetate) (0.3 g, 0.86 mmol) in trifluoroacetic acid (10 mL) and add $N^\alpha$-(carbobenzyloxy)-β-(trifluoroacetyl-allylamino)-L-alanine, methyl ester (105 mg, 0.27 mmol). Stir under an argon atmosphere for 1 hour then evaporate the solvent in vacuo at room temperature. Add methanol and evaporate repeatedly. Purify by silica gel chromatography to give β-(trifluoroacetyl-allylamino)-L-alanine, methyl ester, hydrochloride.

Dissolve β-(trifluoroacetyl-allylamino)-L-alanine, methyl ester, hydrochloride (104.8 g, 0.36 mol) in tetrahydrofuran (300 mL) then cool to 0° C. and add 4-methylmorpholine (88 mL, 0.8 mol). Add, by dropwise addition, a solution of the N-phthaloyl-(S)-phenylalanine, acid chloride (108.7 g, 0.36 mol) in tetrahydrofuran (200 mL). Allow to warm to room temperature and stir for 3 hours. Filter and concentrate the filtrate in vacuo. Dissolve the residue in ethyl acetate and separate the organic phase. Wash with water then saturated sodium chloride and dry ($MgSO_4$). Evaporate the solvent in vacuo to give an oil. Purify by silica gel chromatography to give the title compound.

Scheme E, step b: [S-(R*,R*)]-N-[2-(1,3-Dihydro-1,3-dioxo-2H-isoindol-2-yl)-1-oxo-3-phenylpropyl]-3,4-dihydro-2H-4-trifluoroacetyl-1,4-azazine-3-carboxylic acid, methyl ester Dissolve N-[2-(1,3-dihydro-1,3-dioxo-2H-isoindol-2-yl)-1-oxo-3-phenylpropyl]-(S)-3-[(trifluoroacetyl-2-propenyl)amino]-2-amino-propionic acid, methyl ester (15.8 g, 29.8 mmol) in methylene chloride/methanol (10:1, 220 mL). Cool to −78° C. and sparge with a mixture of ozone/oxygen for approximately 10 minutes until a blue color persists. Sparge with nitrogen for 10 minutes at −78° C. to remove excess ozone. Treat with methyl sulfide (60 mL, 0.82 mol) and allow to warm to room temperature. Stir at room temperature for 2.5 hours, evaporate the solvent in vacuo and dissolve the residue in ethyl acetate (20 0mL). Wash with water, saturated sodium chloride, dry ($MgSO_4$) and evaporate the solvent in vacuo to give the intermediate N-[2-(1,3-dihydro-1,3-dioxo-2H-isoindol-2-yl)-1-oxo-3-phenylpropyl]-N-2-oxoethyl, methyl ester.

Dissolve N-[2-(1,3-dihydro-1,3-dioxo-2H-isoindol-2-yl)-1-oxo-3-phenylpropyl]-(S)-3-[(trifluoroacetyl-2-oxoethyl)amino]-2-amino-propionic acid, methyl ester (15.9 g, 29.8 mmol) in methylene chloride/trifluoroacetic acid (10:1/330 mL). Stir at room temperature for 2.5 hours and evaporate the solvent in vacuo. Purify by silica gel chromatography to give the title compound.

Scheme E, stem c: [4S-[4α, 7α(R*), 12bβ]]-7-[(1,3-Dihydro-1,3-dioxo-2H-isoindol-2-yl)]-3,4,6,7,8,12b-hexahydro-6-oxo-1H-4-trifluoroacetyl-[1,4]-azazino[3,4-a][2]benzazepine-4-carboxylic acid, diphenylmethyl ester Dissolve [S-(R*, R*)]-N-[2-(1,3-dihydro-1,3-dioxo-2H-isoindol-2-yl)-1-oxo-3-phenylpropyl]-3,4-dihydro-2H-4-trifluoroacetyl-1,4-azazine-3-carboxylic acid, methyl ester (3.04 g, 5.9 mmol) in methylene chloride (5 mL) and add, by dropwise addition, to a previously prepared solution of trifluoromethanesulfonic acid (4.0 mL, 45 mmol) and trifluoroacetic anhydride (1.0 mL, 7.1 mmol). Place under a nitrogen atmosphere and stir at room temperature for 123 hours. Pour into a separatory funnel containing ice (200 g) and ethyl acetate (200 mL). Separate the organic phase, wash with water (3×200 mL) and saturated aqueous sodium chloride (100 mL). Extract the organic phase with 10% wt. potassium hydrogen carbonate (4×40 mL) and water (40 mL). Layer the combined basic aqueous phases with ethyl acetate (100 mL) and cool in an ice bath. Add, by dropwise addition, 6N hydrochloric acid to adjust the pH to 1 while maintaining the temperature at 5°–10° C. Separate the organic phase and extract the aqueous phase with ethyl acetate (3×200 mL), wash with saturated sodium chloride and dry (MgSO$_4$). Evaporate the solvent in vacuo and dry the residue under high vacuum at 56° C. for 24 hours to give the intermediate [4S-[4α, 7α(R*),12bβ]]-7-[(1,3-dihydro-1,3-dioxo-2H-isoindol-2-yl)]-3,4,6,7,8,12b-hexahydro-6-oxo-1H-4-trifluoroacetyl-[1,4]-oxazino[3,4-a][2]benzazepine-4-carboxylic acid.

Dissolve [4S-[4α, 7α(R*), 12bβ]]-7-[(1,3-dioxo-2H-isoindol-2-yl)]-3,4,6,7,8,12b-hexahydro-6-oxo-1H-4-trifluoroacetyl-[1,4]-azazino[3,4-a][2]benzazepine-4-carboxylic acid (616 mg, 1.23mmol) in methylene chloride (12 mL) and treat with diphenyl diazomethane (360 mg, 1.86mmol). Stir or 5 5 hours and evaporate the solvent in vacuo. Purify by silica gel chromatography to give the title compound.

Scheme E, step e: [4S-[4α, 7α(R*), 12bβ]]-7-(Amino)-3,4,6,7,8,12b-hexahydro-6-oxo-1H-[1,4]-azazino[3,4a-][2]benzazepine-4-carboxylic acid, diphenylmethyl ester Dissolve [4S-[4α, 7α(R*), 12bβ]]-7-[(1,3-dihydro-1,3-dioxo-2H-isoindol-2-yl)]-3,4,6,7,8,12b-hexahydro-6-oxo-1H-4-trifluoroacetyl-[1,4]-azazino[3,4-a][2]benzazepine-4-carboxylic acid, diphenylmethyl ester (345 mg, 0.51 7 mmol) in methanol (5 mL) and treat with hydrazine monohydrate (1.1 mL of a 1M solution in methanol, 1.1 mmol). Stir at room temperature for 44 hours, evaporate the solvent in vacuo and slurry the residue in methylene chloride (10 mL). Filter and evaporate the solvent in vacuo to give the title compound.

Scheme A: [4S-[4α, 7α(R*), 12bβ]]-7-[(5-Carboxymethyl-5-oxo-2,4,5,6-tetrahydro-cyclopenta[c]pyrrole)methylamino]-3,4,6,7,8,12b-hexahydro-6-oxo-1H-[1,4]-azazino[3,4-a][2]benzazepine-4-carboxylic acid Dissolve 3,4-(dicarboethoxy)pyrrole (1.06 g, 5 mmol) in 50/50 dioxane water (25 mL) and buffer to pH 10 with 1N sodium hydroxide. Add, by dropwise addition, an ether solution of di-t-butyl dicarbonate (1.2 g, 5.5 mmol) at 10° C. Allow to warm to room temperature and buffer occasionally to retain pH 10. Acidify with a sodium citrate/citric acid buffer to pH 5, extract with ethyl ether (3×), dry (MgSO$_4$) and evaporate the solvent in vacuo. Purify the residue by silica gel chromatography to give N-(carbo-t-butyloxy)-3,4-(dicarboethoxy)pyrrole.

Dissolve N-(carbo-t-butyloxy)-3,4-(dicarboethoxy)pyrrole (3.11 g, 10 mmol) in anhydrous tetrahydrofuran (30 mL) and cool to −20° C. Treat with lithium borohydride (7 mL of a 2N solution) and stir under a nitrogen atmosphere for several days. Carefully ad d water and partition between ethyl acetate and 5% hydrochloric acid. Separate the organic phase, wash with brine and dry (MgSO$_4$). Evaporate the solvent in vacuo and purify by silica gel chromatography to give N-(carbo-t-butyloxy)-3,4-(dihydroxymethyl)pyrrole.

Dissolve N-bromosuccinimide (1.78 g, 0.01 mol) in tetrahydrofuran (60 mL) and add a solution of triphenylphosphine (2.62 g, 0.01 mol) in metrahydrofuran. Add a solution of N-(carbo-t-butyloxy)-3,4-(dihydroxymethyl)pyrrole (1.14 g, 5 mmol) in tetrahydrofuran (25 mL) and stir until most of the solid goes into solution. Evaporate the solvent in vacuo and partition the residue between water and ethyl ether. Separate the organic phase and wash with water. Dry (Na$_2$SO$_4$) and evaporate the solvent in vacuo. Purify by silica gel chromatography to give N-(carbo-t-butyloxy)-3,4-(dibromomethyl)pyrrole.

Dissolve diethylmalonate (15.2 mL, 0.100 mol) in tetrahydrofuran (800 mL). Cool in an ice bath and treat with sodium hydride (3.0 g, 0.10 mol, 80% in mineral oil). Stir until solution attained and add N-(t-butyloxy)-3,4-(dibromomethyl)pyrrole (35.3 g, 0.100 mol). Stir for 30 minutes then add additional sodium hydride (3.0 g, 0.10 mol). Stir at room temperature for 20 hours, filter through filter aid and evaporate the solvent in vacuo. Purify by silica gel chromatography to give 5,5-(dicarboethoxy)-2-(carbo-t-butyloxy)-2,4,5,6-tetrahydro-cyclopenta[c]pyrrole.

Dissolve 5,5-(dicarboethoxy)-2-(carbo-t-butyloxy)-2,4,5,6-tetrahydro-cyclopenta[c]pyrrole (21.3 g, 60.6 mmol) in dimethylsulfoxide (140 ml). Add water (14 mL) and lithium chloride (7.0 g, 0.16 mol). Heat at reflux for 4 hours, cool and partition between water (150 mL) and methylene chloride (2×150 mL). Wash the organic phase with water (150 mL), dry (MgSO$_4$) and pass through a silica gel plug to give 5-(carboethoxy)-2-(carbo-t-butyloxy)-2,4,5,6-tetrahydro-cyclopenta[c]pyrrole.

Dissolve 5-(carboethoxy)-2-(carbo-t-butyloxy)-2,4,5,6-tetrahydro-cyclopenta[c]pyrrole (9.5 g, 34.1 mmol) in ethanol (95%, 150 mL) and water (75 mL). Add potassium hydroxide (9.5 g, 0.17 mol) and stir at room temperature for 1 hour. Partition between water (150 mL) and ethyl ether (2×150 mL). Acidify the aqueous phase with hydrochloric acid to pH 1. Extract with methylene chloride (2×150 mL), dry (Na$_2$SO$_4$) and evaporate the solvent in vacuo to give 5-(carboxy)-2-(carbo-t-butyloxy)-2,4,5,6-tetrahydro-cyclopenta[c]pyrrole.

Dissolve 5-(carboxy)-2-(carbo-t-butyloxy)-2,4,5,6-tetrahydro-cyclopenta[c]pyrrole (5.9 g, 23.5mmol) in methanol (60 mL) and treat with dimethoxypropane (5.8 mL, 47 mmol) and sulfuric acid (0.8 mL). Stir at room temperature for 1 day. Evaporate the solvent in vacuo, dilute with methylene chloride (75 mL) and wash with saturated sodium hydrogen carbonate (35 mL). Extract the aqueous phase with methylene chloride (30 mL), wash combined organics with brine (30 mL) and dry (Na$_2$SO$_4$). Evaporate the solvent in vacuo and pass through a plug of silica gel to give 5-(carbomethoxy)-2-(carbo-t-butyloxy)-2,4,5,6-tetrahydro-cyclopenta[c]pyrrole.

Dissolve diisopropylamine (3.5 mL, 25 mmol) in tetrahydrofuran (30 mL). Add n-butyllithium (14 mL of a 1.6M solution in hexane, 22.4 mmol). Stir for 15 minutes and cool to −78° C. Add, by dropwise addition, 5-(carbomethoxy)-2-(carbo-t-butyloxy)- 2,4,5,6-tetrahydro-cyclopenta[c]pyrrole (5.3 g, 20 mmol) and stir for 30 minutes. Add t-butyl bromoacetate (4.0 mL, 25 mmol) and gradually warm to room temperature overnight. Quench the solution with ammonium chloride solution (10 mL) and partition between water (25 mL) and ethyl ether (50 mL). Separate the organic phase, dry (MgSO$_4$) and evaporate t he solvent in vacuo. Purify by silica gel chromatography to give 5-(carbomethoxy)-5-(carbo-t-butyloxymethyl)-2-(carbo-t-butyloxy)-2,4,5,6-tetrahydro-cyclopenta[c]pyrrole.

Dissolve 5-(carbomethoxy)-5-(carbo-t-butyloxymethyl)-2-(carbo-t-butyloxy)-2,4,5,6-tetrahydro-cyclopenta[c]pyrrole (2.92 g, 9.17 mmol) in ethanol (95% 60 mL) and water (30 mL) Treat with potassium hydroxide (2.94 g, 52 mmol). Stir at room temperature for 3 hours. Add water (75 mL) and extract with ethyl ether (2×50 mL). Extract the combined ethereal phases with water (75 mL) and acidify the combined aqueous phases with aqueous 1M tartaric acid (pH 2–3). Extract with ethyl acetate (2×125 mL), dry (Na$_2$SO$_4$) and evaporate the solvent in vacuo. Take the residue up in methylene chloride and filter to give 5-(carboxy)-5-(carbo-t-butyloxymethyl)-2-(carbo-t-butyloxy)-2,4,5,6-tetrahydro-cyclopenta[c]pyrrole.

Dissolve [4S-[4α, 7α(R*), 12bβ]]-7-(amino)-3,4,6,7,8,12b-hexahydro-6-oxo-1H-[1,4]-azazino[3,4-a][2]benzazepine-4-carboxylic acid, diphenylmethyl ester (200 mg, 0.454 mmol) and EDC (130 mg, 0.68 mmol) in tetrahydrofuran (5 mL). Treat with 5-(carboxy)-5-(carbo-t-butyloxymethyl)-2-(carbo-t-butyloxy)-2,4,5,6-tetrahydro-cyclopenta[c]pyrrole (166 mg, 0.454 mmol). Stir at room temperature for 20 hours and evaporate the solvent in vacuo. Dissolve the residue in ethyl acetate (50 mL) and wash with 5% sulfuric acid (15 ml) then saturated sodium hydrogen carbonate (15 mL). Dry (Na$_2$SO$_4$) and evaporate the solvent in vacuo. Purify by silica gel chromatography to give [4S-[4α, 7α(R*), 12bβ]]-7-[(5-(carbo-t-butyloxymethyl)-5-oxo-2-(carbo-t-butyloxy)-2,4,5,6-tetrahydro-cyclopenta[c]pyrrole)methylamino]3,4,6,7,8,12b-hexahydro-6-oxo-1H-[1,4]-azazino[3,4-a][2]benzazepine-4-carboxylic acid, diphenylmethyl ester.

Dissolve [4S-[4α, 7α(R*), 12bβ]]-7-[(5-(carbo-t-butyloxymethyl)-5-oxo-2-(carbo-t-butyloxy)-2,4,5,6-tetrahydro-cyclopenta[c]pyrrole)methylamino]-3,4,6,7,8,12b-hexahydro-6-oxo-1H-[1,4]-azazino[3,4-a][2]benzazepine-4-carboxylic acid, diphenylmethyl ester (128 mg, 0.163 mmol) in methylene chloride (3 mL) and treat with anisole (0.19 mL, 1.7 mmol). Cool in an ice-methanol bath and add trifluoroacetic acid (0.8 mL, 10 mmol) and stir for 2.5 hours at 0° C. Partition between ethyl acetate (25 mL) and brine (15 mL). Separate the organic phase and wash with brine (15 mL). Dry (Na$_2$SO$_4$), evaporate the solvent in vacuo and purify by silica gel chromatography to give the title compound.

EXAMPLE 12

Preparation of [4S-[4α, 7α(R*), 12bβ]]-7-[(5-Carboxymethyl-5-oxo-2,4,6-tetrahydro-cyclopenta[c]pyrrole)methylamino]-3,4,6,7,8,12b-hexahydro-6-oxo-1H-[1,4]-N4-trifluoroacetyl-azazino[3,4-a][2]benzazepine-4-carboxylic acid Dissolve [4S-[4α, 7α(R*), 12bβ]]-7-[(5-(carbo-t-butyloxymethyl)-5-oxo-2-(carbo-t-butyloxy)-2,4,5,6-tetrahydro-cyctopenta[c]pyrrole)methylamino]-3,4,6,7,8,12b-hexahydro-6-oxo-1H-[1,4]-azazino[3,4-a][2]benzazepine-4-carboxylic acid, diphenyl methyl ester (1.79 g, 2.27 mmol) in anhydrous tetrahydrofuran (15 mL). Treat with pyridine (183 μL, 2.27 mmol) followed by trifluoroacetic anhydride (321 μL, 2.27 mmol) and stir at room temperature overnight. Partition between ethyl ether and water. Separate the organic phase, dry (MgSO$_4$) and evaporate the solvent in vacuo. Purify by silica gel chromatography to give [4S-[4α, 7α(R*), 12bβ]]-7-[(5-(carbo-t-butyloxymethyl)-5-oxo-2-(carbo-t-butyloxy)-2,4,5,6-tetrahydro-cyclopenta[c]pyrrole)methylamino]- 3,4,6,7,8,12b-hexahydro-6-oxo-1H-[1,4]-N$^4$-trifluoroacetyl-azazino[3,4-a][2]benzazepine-4-carboxylic acid, diphenylmethyl ester.

Dissolve [4S-[4α, 7α(R*), 12bβ]]-7-[(5-(carbo-t-butyloxymethy)-5-oxo-2-(carbo-t-butyloxy)-2,4,5,6-tetrahydro-cyclopenta[c]pyrrole)methylamino]-3,4,6,7,8,12b-hexahydro-6-oxo-1H-[1,4]-N$^4$-trifluoroacetyl-azazino[3,4-a][2]benzazepine-4-carboxylic acid, diphenyimethyl ester (141 mg, 0.163 mmol) in methylene chloride (3 mL) and treat with anisole (0.19 mL, 1.7 mmol). Cool in an ice-methanol bath and add trifluoroacetic acid (0.8 mL, 10 mmol) and for 2.5 hours at 0° C. Partition between ethyl acetate (25 mL) and brine (15 mL). Separate the organic phase and wash with brine (15 mL). Dry (Na$_2$SO$_4$), evaporate the solvent in vacuo and, purify by silica gel chromatography to give the title compound.

EXAMPLE 13

[6α(R*), 11bβ]-6-[(S)-(5-Carboxymethyl-5-oxo-2,4,5,6-tetrahydro-cyclopenta[c]pyrrole)methylamino]-1,2,3,5,6,7,11b-heptahydro-5-oxo-pyrrolo[2,1-a][2]benzazepine-3(S)-carboxylic acid, methyl ester Scheme G, step a: N-(Phenylmethylene)-2-(3-butenyl)glycine methyl ester Dissolve diisopropylamine (15.4 mL, 110 mmol) in tetrahydrofuran (250 mL), place under a nitrogen atmosphere and cool to −78° C. Add n-butyllithium (39 mL of a 2.7M solution in hexane, 105 mmol). Stir for 30 minutes and add, by dropwise addition, a solution of N-(phenylmethylene)glycine methyl ester (17.7 g, 100 mmol) in tetrahydrofuran (25 mL). Stir for 15 minutes and add 4-bromobutene (13.5 g, 100 mmol) and allow to warm slowly to room temperature. Add hexamethylphosmhoramide (20 mL, 100 mmol) and stir under a nitrogen atmosphere for 3 hours. Pour into water, extract into ethyl ether and wash with brine several times. Dry (MgSO$_4$) and evaporate the solvent in vacuo to give the title compound as an amber oil (25 g).

Scheme G, step b: 2-(3-butenyl)glycine methyl ester
Dissolve N-(phenylmethylene)-2-(3-butenyl)glycine methyl ester (25 g) in ethyl ether (400 mL) and stir with 1N hydrochloric acid (150 mL) and water (150 mL). Place under an argon atmosphere and stir for 2 hours. Separate the aqueous phase and adjust to pH 9, extract into chloroform, dry and evaporate the solvent in vacuo to give the title compound as a light oil (4.5 g).

Scheme G, step c: (S)-N-[2-(1,3-Dihydro-1,3-dioxo-2H-isoindol-2-yl)-1-oxo-3-phenylpropyl]2-(3-butenyl)-glycine, methyl esters Dissolve N-phthaloyl-(S)-phenylalanine (2) (6.0 g, 20 mmol) and EEDQ (6.0 g, 24 mmol) in methylene chloride (30 mL). Add 2-(3-butenyl)glycine methyl ester (3.0 g, 21 mmol) and stir for 18 hours. Pour into methylene chloride, wash with 10% hydrochloric acid (2×100 mL) then saturated sodium hydrogen carbonate. Dry and evaporate the solvent in vacuo to give 8.3 g yellow oil. Purify by silica gel chromatography (25% ethyl acetate/hexane) to give a diastereomeric mixture of the title compounds as foam (5.2 g).

Scheme G, step d: (S)-N-[2-(1,3-Dihydro-1,3-dioxo-2H-isoindol-2-yl)]-(S)-phenylalanyl]-2-(3-oxopropyl)glycine, methyl esters Dissolve the diastereomeric mixture of (S)-N-[2-(1,3-dihydro-1,3-dioxo-2H-isoindol-2-yl)-1-oxo-3-phenylpropyl]-2-(3-butenyl)-glycine, methyl esters (4.2 g, 10 mmol) in methylene chloride (100 mL) and absolute methanol (10 mL). Cool to −78° C. and treat with ozone until blue. Degas with oxygen and add methyl sulfide (10 mL) and pyridine (0.5 mL). Allow to warm slowly to room temperature and stir for 18 hours. Wash with 10% hydrochloric acid then brine. Dry and evaporate the solvent in vacuo to give a diastereomeric mixture of the title compounds as an oil (4.5 g).

Scheme F, step c: (S)-N-[2-(1,3-Dihydro-1,3-dioxo-2H-isoindol-2-yl)]-1-oxo-3-phenylpropyl-1,2,3-trihydro-2(S)-pyrrolecarboxylic acid, methyl ester and (S)-N-[2-(1,3-Dihydro-1,3-dioxo-2H-isoindol-2-yl)]-1-oxo-3-phenylpropyl-1,2,3-trihydro-2(R)-pyrrolecarboxylic acid, methyl ester Dissolve the diastereomeric mixture of (S)-N-[2-(1,3-dihydro-1,3-dioxo-2H-isoindol-2-yl)]-(S)-phenylalanyl]-2-(3-oxopropyl)glycine, methyl esters (4.5 g) in 1,1,1-trichloroethane (150 mL) and treat with trifluoroacetic acid (0.5 mL). Heat at reflux for 18 hours, evaporate the solvent and purify by silica gel chromatography (80% ethyl acetate/hexane) to give the 2(S)-title compound (700 mg) and the 2(R)-title compound (600 mg).

Scheme F, Step d: [6α(R*), 11bβ]-6-[(S)-(1,3-Dihydro-1,3-dioxo-2H-isoindol-2-yl)]-1,2,3,5,6,7,11b-heptahydro-5-oxo-pyrrolo[2,1a][2]benzazepine-3(S)-carboxylic acid, methyl ester Dissolve (S)-N-[2-(1,3-dihydro-1,3-dioxo-2H-isoindol-2-yl)]-1-oxo-3-phenylpropyl-1,2,3-trihydro-2(S)-pyrrolecarboxylic acid, methyl ester (338 mg, 0.836 mmol) in anhydrous methylene chloride (10 mL) and add to trifluoromethanesulfonic acid (5 mL). Stir for 3.5 hours, cool in an ice bath and carefully add water (25 mL). Extract with ethyl acetate (75 mL) and wash with saturated sodium hydrogen carbonate (25 mL). Dry (Na$_2$SO$_4$) and evaporate the solvent in vacuo. Purify by silica gel chromatography (1:1 ethyl acetate/hexane to 2:1 ethyl acetate/hexane) to give the title compound as a white foam (314 mg, 93%).

Scheme F Step e: [6α(R*), 11bβ]-6-[(S)-Amino]-1,2,3,5,6,7,11b-heptahydro-5-oxo-pyrrolo[2,1-a][2]benzazepine-3(S)-carboxylic acid, methyl ester Dissolve [6α(R*), 11bβ]-6-[(S)-(1,3-dihydro-1,3-dioxo-2-H-isoindol-2-yl)]-1,2,3,5,6,7,11b-heptahydro-5-oxo-pyrrolo[2,1-a][2]benzazepine-3(S)-carboxylic acid, methyl ester (244 mg, 0.603 mmol) in methanol (3 mL) and treat with hydrazine monohydrate (0.70 mL of a 1M solution in methanol) and stir at room temperature for 24 hours. Add additional hydrazine monohydrate (0.3 mL of a 1M solution in methanol) and stir for 48 hours. Filter through filter aid, evaporate the solvent in vacuo and add methylene chloride. Filter slowly through a mixture of filter aid and MgSO$_4$ then evaporate the solvent in vacuo to give the title compound as a yellow oil (181 mg).

Scheme A: [6α(R*), 11bβ]-6-[(S)-(5-Carboxymethyl-5-oxo-2,4,5,6-tetrahydro-cyclopenta[c]pyrrole)methylamino]-1,2,3,5,6,7,11b-heptahydro-5-oxo-pyrrolo[2,1-a][2]benzazepine-3(S)-carboxylic acid, methyl ester Dissolve 5-(carboxy)-2-(carbo-t-butyloxy)-5-(carbo-t-butyloxymethyl)-2,4,5,6-tetrahydro-cyclopenta[c]pyrrole (308 mg, 0.845 mmol) in methylene chloride (6 mL), cool in an ice-methanol bath and treat with oxalyl chloride (0.94 mL, 11 mmol). Stir for 1.5 hours, evaporate the solvent in vacuo at 0°–5° C. Dilute the residue with methylene chloride (3 mL) and add a solution of [6α(R*), 11bβ]-6-[(S)-amino]-1,2,3,5,6,7,11b-heptahydro-5-oxo-pyrrolo[2,1-a][2]benzazepine-3(S)-carboxylic acid, methyl ester (155 mg, 0.565 mmol) in methylene chloride (6 mL). Add pyridine (68 μL, 0.85 mmol) and stir for 2 hours. Dilute with ethyl acetate (60 mL) and wash with 1N hydrochloric acid (30 mL) and saturated sodium hydrogen carbonate (2×30 mL). Dry (MgSO$_4$), evaporate the solvent in vacuo and purify by silica gel chromatography to give [6α(R*), 11bβ]-6-[(S)-(5-(carbo-t-butyloxymethy)-5-oxo-2-(carbo-t-butyloxy)-2,4,5,6-tetrahydro-cyclopenta[c]pyrrole)methylamino]-1,2,3,5,6,7,11b-heptahydro-5-oxo-pyrrolo[2,1-a][2]benzazepine-3(S)-carboxylic acid, methyl ester.

Dissolve [6α(R*), 11bβ]-6-[(S)-(5-(carbo-t-butyloxymethyl)-5-oxo-2-(carbo-t-butyloxy)-2,4,5,6-tetrahydro-cyclopenta[c]pyrrole)methylamino]-1,2,3,5,6,7,11b-heptahydro-5-oxo-pyrrolo[2,1-a][2]benzazepine-3(S)-carboxylic acid, methyl ester (101 mg, 0.163 mmol) in methylene chloride (3 mL) and treat with anisole (0.19 mL, 1.7 mmol). Cool in an ice-methanol bath and add trifluoroacetic acid (0.8 mL, 10 mmol) and stir for 2.5 hours at 0° C. Partition between ethyl acetate (25 mL) and brine (15 mL). Separate the organic phase and wash with brine (15 mL). Dry (Na$_2$SO$_4$), evaporate the solvent in vacuo and purify by silica gel chromatography to give the title compound.

EXAMPLE 14

Preparation of [6α(R*), 11bβ]-6-[(S)-(5-Carboymethyl-5-oxo-2,4,5,6-tetrahydro-cyclopenta[c]pyrrole)methylamino]-1,2,3,5,6,7,11b-heptahydro-5-oxo-pyrrolo[2,1-a][2]benzazepine-3(S)-carboxylic acid Dissolve [6α(R*), 11bβ]-6-[(S)-(5-carboxymethyl-5-oxo-2,4,5,6-tetrahydro-cyclopenta[c]pyrrole)methylamino]-1,2,3,5,6,7,11b-heptahydro-5-oxo-pyrrolo[2,1-a][2]benzazepine-3(S)-carboxylic acid, methyl ester (46 mg, 0.098 mmol) in methanol (1.5 mL) at 0° C. and add aqueous 1N lithium hydroxide (0.6 mL, 0.6 mmol) at 0° C. Add tetrahydrofuran to obtain solution (4 mL) and stir for 17 hours at room temperature, cool in an ice bath and add 1N hydrochloric acid (1 mL). Partition between methylene chloride (30 mL) and water (15 mL) and separate the organic phase. Dry (Na$_2$SO$_4$), evaporate the solvent in vacuo and purify by silica gel chromatography to give the title compound.

In a further embodiment, the present invention provides a method of inhibiting enkephalinase in a patient in need thereof comprising administering to said patient an effective enkephalinase inhibitory amount of a compound of Formula (I).

As used herein, the term "patient" refers to warm-blooded animals or mammals, including mice, rats and humans. A patient is in need of treatment to inhibit enkephalinase when the patient is suffering from acute or chronic pain and is in need of an endorphin- or enkephalin-mediated analgesic effect. In addition, a patient is in need of treatment to inhibit enkephalinase when the patient is suffering from a disease state characterized by abnormalities in fluid, electrolyte, blood pressure, intraocular pressure, renin, or aldosterone homeostasis, such as, but not limited to, hypertension, renal diseases, hyperaldosteronemia, cardiac hypertrophy, glaucoma and congestive heart failure. In these instances the patient is in need of an ANP-mediated diuretic, natriuretic, hypotensive, hypoaldosteronemic effect. Inhibition of enkephalinase would provide an endorphin- or enkephalin-mediated analgesic effect by inhibiting the metabolic degradation of endorphans and enkephalins. Inhibition of enkephalinase would provide an ANP-mediated diuretic, natriuretic, hypotensive, hypoaldosteronemic effect by inhibiting the metabolic degradation of ANP. Inhibition of enkephalinase would also potentiate endogenous levels of bradykinin. Inhibition of enkephalinase would also modulate intestinal smooth muscle contractility and would be useful in the treatment of irritable bowel syndrome.

In addition, a patient is in need of treatment to inhibit enkephalinase when the patient is in need of an antidepressant effect or a reduction in severity of withdrawal symptoms associated with termination of opiate or morphine administration.

The identification of those patients who are in need of treatment to inhibit enkephalinase is well within the ability and knowledge of one skilled in the art. A clinician skilled in the art can readily identify, by the use of clinical tests, physical examination and medical/family history, those patients who are in need of an endorphin- or enkephalin-mediated analgesic effect or who are in need of an ANP-mediated diuretic, natriuretic, hypotensive or hypoaldosteronemic effect.

An effective enkephalinase inhibitory amount of a compound of Formula (I) is an amount which is effective in inhibiting enkephalinase and in thus inhibiting the metabolic degradation of the naturally-occurring circulating regulatory peptides such as the endorphins, including enkephalins, and ANP. Successful treatment is also understood to include prophylaxis in treating a patient in those instances such as, for example, in a pre-operative procedure, where a patient will be suffering from acute or chronic pain in the near future.

An effective enkephalinase inhibitory amount of a compound of Formula (I) is an amount which is effective in inhibiting enkephalinase in a patient in need thereof which results, for example, in endorphin- or enkephalin-mediated analgesic effects or in ANP-mediated diuretic, natriuretic, hypotensive, hypoaldosteronemic effect.

An effective enkephalinase inhibitory dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective enkephalinase inhibitory amount of a compound of Formula (I) will generally vary from about 0.01 milligram per kilogram, of body weight per day (mg/kg/day) to about 20 mg/kg/day. A daily dose of from about 0.1 mg/kg to about 10 mg/kg is preferred.

In addition the present invention further provides a method of inhibiting ACE in a patient in need thereof comprising administering to said patient an effective ACE inhibitory amount of a compound of Formula (I). A patient is in need of treatment to inhibit ACE when the patient is suffering from hypertension, chronic congestive heart failure, hyperaldosteronemia or cognitive disorders. Inhibition of ACE reduces levels of angiotensin II and thus inhibits the vasopressor, hypertensive and hyperaldosteronemic effects caused thereby. An effective ACE inhibitory amount of a compound of Formula (I) is that amount which is effective in inhibiting ACE in a patient in need thereof which results, for example, in a hypotensive effect. An effective ACE inhibitory amount and an effective ACE inhibitory dose are the same as that described above for an effective enkephalinase inhibitory amount and dose.

In addition, the present invention further provides a method for treating a patient suffering from smooth cell proliferation. An effective smooth cell proliferation inhibitory amount of a compound of Formula (I) is that amount which is effective in inhibiting smooth cell proliferation in a patient in need thereof which results, for example, in a reduced myointimal thickening after vascular injury. An effective smooth cell proliferation inhibitory amount and an effective smooch cell proliferation inhibitory dose are the same as that described above for an effective enkephalinase inhibitory amount and dose.

In effecting treatment of a patient, compounds of Formula (I) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing Formulations can readily select the proper form and mode of administration depending upon the disease state to be treated, the stage of the disease, and other relevant circumstances.

Compounds of Formula (I) can be administered in the form of pharmaceutical compositions or medicaments which are made by combining the compounds of Formula (I) with pharmaceutically acceptable carriers or excipients, the proportion and nature of which are determined by the chosen route of administration, and standard pharmaceutical practice.

In another embodiment, the present invention provides compositions comprising a compound of Formula (I) in admixture or otherwise in association with one or more inert carriers. These compositions are useful, for example, as assay standards, as convenient means of making bulk shipments, or as pharmaceutical compositions. An assayable amount of a compound of Formula (I) is an amount which is readily measurable by standard assay procedures and techniques as are well known and appreciated by those skilled in the art. Assayable amounts of a compound of Formula (I) will generally vary from about 0.001% to about 75% of the composition by weight, inert carriers can be any material which does not degrade or otherwise covalently react with a compound of Formula (I). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising an effective amount of a compound of Formula (I) in admixture or otherwise in association with one or more pharmaceutically acceptable carriers or excipients.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, the compounds of Formula (I) may be incorporated with excipients and used in the form of tablets, troches, capsules, elixirs, suspensions, syrups, wafers, chewing gums and the like. These preparations should contain at least 4% of the compound of Formula (I), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotax; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, the compounds of Formula (I) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfize; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

As with any group of structurally related compounds which possess a particular generic utility, certain groups and configurations are preferred for compounds of Formula (I) in their end-use application.

The compounds of Formula (1) wherein $B_1$ is hydrogen or alkoxy are preferred. The compounds of Formula (1) wherein $B_2$ is hydrogen or alkoxy are preferred. Compounds of Formula (1) wherein $R_1$ and $R_3$ are hydrogen and n is 0 are preferred.

It is, of course, understood that the compounds of Formula (I) may exist in a variety of isomeric configurations including structural as well as stereo isomers. It is further understood that the present invention encompasses those compounds of Formula (I) in each of their various structural and stereo isomeric configurations as individual isomers and as mixtures of isomers.

The following specific compounds of Formula (1) are particularly preferred in the end-use application of the compounds of the present invention:

[4S-[4α, 7α(R*), 12bβ]]-7-[(2-carboxymethyl-2-oxoindan)methylamino]-1,2,3,4,6,7,8,12b-octahydro-6-oxopyrido[2,1-a][2]benzazepine-4-carboxylic acid;

[4S-[4α, 7α(R*), 12bβ]]-7-[(2-pivaloyloxymethylcarboxymethy-2-oxoindan)methylamino]- 1,2,3,4,6,7,8, 12b-octahydro-6-oxopyrido[2,1-a][2]benzazepine-4-carboxylic acid;

[4S-[4α, 7α(R*), 12bβ]]-7-[(2-carboxymethyl-2-oxoindan)methylamino]-1,2,3,4,6,7,8,12b-octahydro-6-oxopyrido[2,1-a][2]benzazepine-4-carboxylic acid, pivaloyloxymethyl ester;

[4S-[4α, 7α(R*), 12bβ]]-7-[(2-pivaloyloxymethylcarboxymethyl-2-oxoindan)methylamino]-1,2,3,4,6,7,8, 12b-octahydro-6-oxopyrido[2,1-a][2]benzazepine-4-carboxylic acid, pivaloyloxymethyl ester.

The following studies illustrate the utility of the compounds of the present invention as enkephalinase inhibitors and as ACE inhibitors.

Enkephalinase is partially purified from rat kidney. The enzyme is extracted from the microvilli fraction by using Triton X-100 according to the method of Malfroy and Schwartz [*J. Biol. Chem.* 259, 14365–14370 (1984)] or by using a proteolytic treatment according to the method of Almenoff and Orlowski [*Biochem.* 22, 590 –599 (1983)]. The enzyme is further purified by anion exchange chromatography (Mono Q™ column, Pharmacia) using a Pharmacia FPLC system. The enzyme activity may be measured by the fluorometric methods of Florentin et al. [*Anal. Biochem.* 141, 62–69 (1984)] or of Almenoff and Orlowski [*J. Neurochemistry* 42, 151–157 (1984)]. The enzyme is assayed in 50 mM HEPES buffer (pH 7.4) in a 3.0 mL reaction volume containing 12 μM of the substrate dansyl-D-AlaGly(p-nitro-)PheGly ($K_m$=40 μM) at 25° C. The substrate (and inhibitor) is added from a concentrated stock solution in DMSO (up to 0.1 mL DMSO final volume). The enzyme in a small volume (approximately 0.1 μg of FPLC purified protein) is added to initiate the reaction and the rate of fluorecense increase is recorded continuously using a fluorometer (excitation at 339 nm, emission at 562 nm).

The enzymatic activity of ACE is monitored using the spectrophotometric substrate described by Hoimquist et al. [*Anal. Biochem.* 95, 540–548 (1979)] and the buffer system described by Ryan [*Methods of Enzymatic Analysis*, 3rd ed., H. U. Bergmeyer, editor; vol. V, Verlag Chemic, Weinheim, 1983, pp. 20–34].

The results of the analysis of enzymatic activity as described in Table 1 indicate that the compounds of the present invention are inhibitors of enkephalinase as well as inhibitors of ACE.

TABLE 1

$K_i$'s of Compounds of Formula (I) as Inhibitors of Enkephalinase and of ACE

| Compound of Formula (1) | Enkephalinase, $K_i$ (nM) | ACE, $K_i$ (nM) |
|---|---|---|
| 102,353 | <0.2 | <104 |
| 101,137 | 0.4 | |

102,353 = [4S-[4α, 7α(R*), 12bβ]]-7-[(2-Carboxymethyl-2-oxoindan)methylamino]-1,2,3,4,6,7,8,12b-octahydro-6-oxopyrido[2,1-a][2]benzazepine-4-carboxylic acid 100,137 = [4S-[4α, 7α(R*), 12bβ]]-7-[(1-Carboxymethyl-1-oxocyclopentane)methylamino]-1,2,3,4,6,7,8,12b-octahydro-6-oxopyrido[2,1-a][2]benzazepine-4-carboxylic acid

What is claimed is:

1. A method of inhibiting enkephalinase in a patient in need thereof comprising administering to said patient an effective enkephalinase inhibitory amount of a compound of the formula

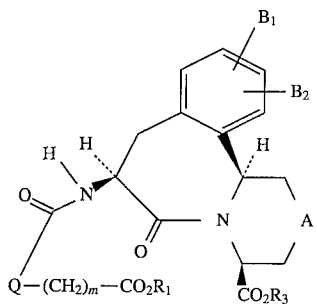

wherein

B₁ and B₂ are each independently hydrogen; hydroxy; —OR₂ wherein R₂ is a $C_1$-$C_4$ alkyl or an Ar—Y group wherein Ar is aryl and Y is a hydrogen or $C_1$-$C_4$ alkyl; or, where B₁ and B₂ are attached to adjacent carbon atoms, B₁ and B₂ can be taken together with said adjacent carbons to form a benzene ring or methylenedioxy;

A is a bond, methylene, oxygen, sulfur, NR₄ or NCOR₅ wherein R₄ is hydrogen, a $C_1$-$C_4$ alkyl or an Ar—Y— group and R₅ is —CF₃ or a $C_1$-$C_{10}$ alkyl or an Ar—Y group;

R₃ is hydrogen or —CH₂OC(O)C(CH₃)₃;

R₁ is hydrogen, $C_1$-$C_4$ alkyl, or —CH₂OC(O)C(CH₃)₃;

m is an integer 1 to 3; and

Q is a group of the formula

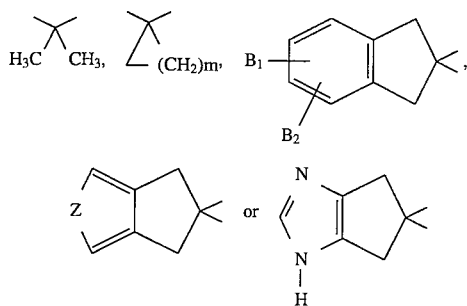

wherein

Z is O, NH or S; and m is an integer 1 to 5.

2. A method according to claim 1 wherein the patient is in need of an endorphin- or enkephalin-mediated analgesic effect.

3. A method according to claim 1 wherein the patient is in need of an ANP-mediated hypotensive effect.

4. A method according to claim 1 wherein the patient is in need of an ANP-mediated diuretic effect.

5. A method according to claim 1 wherein the patient is suffering from congestive heart failure.

6. A method according to claim 1 wherein the patient suffering from irritable bowel syndrome.

7. A method of inhibiting ACE in a patient in need thereof comprising administering to said patient an effective ACE inhibitory amount of a compound of the formula

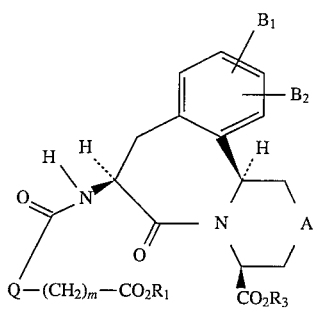

wherein

B₁ and B₂ are each independently hydrogen; hydroxy; —OR₂ wherein R₂ is a $C_1$-$C_4$ alkyl or an Ar—Y group wherein Ar is aryl and Y is a hydrogen or $C_1$-$C_4$ alkyl; or, where B₁ and B₂ are attached to adjacent carbon atoms, B₁ and B₂ can be taken together with said adjacent carbons to form a benzene ring or methylenedioxy;

A is a bond, methylene, oxygen, sulfur, NR₄ or NCOR₅ wherein R₄ is hydrogen, a $C_1$-$C_4$ alkyl or an Ar—Y— group and R₅ is —CF₃ or a $C_1$-$C_{10}$ alkyl or an Ar—Y group;

R₃ is hydrogen or —CH₂OC(O)C(CH₃)₃;

R₁ is hydrogen, $C_1$-$C_4$ alkyl, or —CH₂OC(O)C(CH₃)₃;

m is an integer 1 to 3; and

Q is a group of the formula

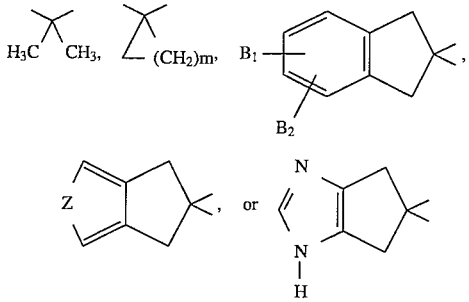

wherein

Z is O, NH or S; and m is an integer 1 to 5.

8. A method according to claim 7 wherein the patient is in need of a hypotensive effect.

9. A method according to claim 7 wherein the patient is in need of a cognition enhancing effect.

10. A method according to claim 7 wherein the patient is suffering from congestive heart failure.

11. A method of inhibiting smooth cell proliferation in a patient in need thereof comprising administering to said patient an effective smooth cell proliferation inhibitory amount of a compound of the formula wherein B₁ and B₂ are each independently hydrogen; hydroxy; —OR₂ wherein R₂ is a $C_1$-$C_4$ alkyl or an Ar—Y group wherein Ar is aryl and Y is a hydrogen or $C_1$-$C_4$ alkyl; or, where B₁ and B₂ are attached to adjacent carbon atoms, B₁ and B₂ can be taken together with said adjacent carbons to form a benzene ring or methylenedioxy;

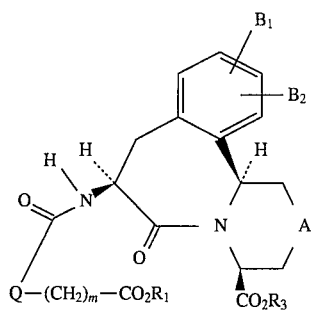
- A is a bond, methylene, oxygen, sulfur, NR₄ or NCOR₅ wherein R₄ is hydrogen, a C₁–C₄ alkyl or an Ar—Y— group and R₅ is —CF₃ or a C₁–C₁₀ alkyl or an Ar—Y group;
- R₃ is hydrogen or —CH₂OC(O)C(CH₃)₃;
- R₁ is hydrogen, C₁–C₄ alkyl, or —CH₂OC(O)C(CH₃)₃;
- m is an integer 1 to 3; and
Q is a group of the formula
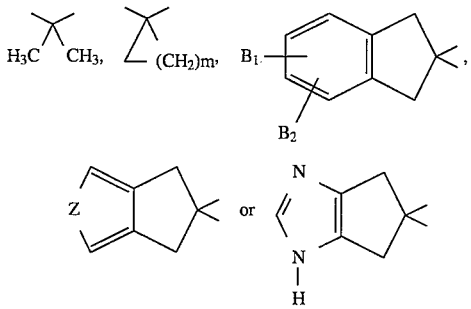
wherein
Z is O, NH or S; and
m is an integer 1 to 5.
* * * * *